United States Patent
Lee et al.

(10) Patent No.: US 12,343,537 B2
(45) Date of Patent: *Jul. 1, 2025

(54) NEUROSTIMULATION FOR TREATING SENSORY DEFICITS, AND ASSOCIATED SYSTEMS AND METHODS

(71) Applicant: Nevro Corp., Redwood City, CA (US)

(72) Inventors: Dongchul Lee, Agua Dulce, CA (US); Kerry Bradley, Glendale, CA (US); Kwan Yeop Lee, Poway, CA (US)

(73) Assignee: Nevro Corporation, Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/637,299

(22) Filed: Apr. 16, 2024

(65) Prior Publication Data

US 2025/0041601 A1    Feb. 6, 2025

Related U.S. Application Data

(63) Continuation of application No. 18/344,579, filed on Jun. 29, 2023, now Pat. No. 11,986,657.

(60) Provisional application No. 63/357,798, filed on Jul. 1, 2022.

(51) Int. Cl.
*A61N 1/36* (2006.01)

(52) U.S. Cl.
CPC ..... *A61N 1/36062* (2017.08); *A61N 1/36171* (2013.01); *A61N 1/36157* (2013.01); *A61N 1/36175* (2013.01)

(58) Field of Classification Search
CPC ............ A61N 1/36062; A61N 1/36171; A61N 1/36157; A61N 1/36175
See application file for complete search history.

(56) References Cited

U.S. PATENT DOCUMENTS

| | | |
|---|---|---|
| 6,721,603 B2 | 4/2004 | Zabara et al. |
| 6,871,099 B1 | 3/2005 | Whitehurst et al. |
| 7,162,304 B1 | 1/2007 | Bradley |
| 8,569,935 B1 | 10/2013 | Kosierkiewicz |
| 8,712,533 B2 | 4/2014 | Alataris |
| 8,768,472 B2 | 7/2014 | Fang |
| 8,903,501 B2 | 12/2014 | Perryman et al. |
| 8,918,190 B2 | 12/2014 | Libbus et al. |

(Continued)

FOREIGN PATENT DOCUMENTS

| | | |
|---|---|---|
| JP | 2018500143 | 1/2018 |
| JP | 2013521979 | 5/2021 |

(Continued)

OTHER PUBLICATIONS

Ahmed et al., "Effects of Spinal Cord Stimulation on Pain Thresholds and Sensory Perceptions in Chronic Pain Patients," Neuromodulation. 2015;18(5):6 pages.

(Continued)

*Primary Examiner* — Paula J Stice

(57) ABSTRACT

Stimulation for treating sensory deficits in patients with spinal cord injuries and/or peripheral polyneuropathy, and associated systems and methods. A representative method includes addressing the patient's somatosensory dysfunction, resulting from neuropathy and/or spinal cord injury, by directing an electrical therapy signal to the patient's spinal cord region, the therapy signal having a frequency in a frequency range from 200 Hz to 100 KHz.

26 Claims, 10 Drawing Sheets

(56) References Cited

U.S. PATENT DOCUMENTS

| | | |
|---|---|---|
| 8,954,153 B2 | 2/2015 | Boggs, II |
| 9,002,477 B2 | 4/2015 | Burnett |
| 9,295,841 B2 | 3/2016 | Fang et al. |
| 9,327,121 B2 | 5/2016 | Thacker |
| 9,387,338 B2 | 7/2016 | Burnett |
| 9,452,286 B2 | 9/2016 | Cowan et al. |
| 9,486,632 B2 | 11/2016 | Saab |
| 9,486,633 B2 | 11/2016 | Kramer et al. |
| 9,533,149 B2 | 1/2017 | Lee et al. |
| 9,561,371 B2 | 2/2017 | Elborno |
| 9,630,011 B2 | 4/2017 | Lipani |
| 9,757,584 B2 | 9/2017 | Burnett et al. |
| 9,782,589 B2 | 10/2017 | Oron et al. |
| 9,789,313 B2 | 10/2017 | Lipani |
| 9,833,614 B1 | 12/2017 | Gliner |
| 9,861,547 B2 | 1/2018 | Crunick et al. |
| 9,884,189 B2 | 2/2018 | Boggs, II |
| 9,895,530 B2 | 2/2018 | Boggs, II |
| 9,895,539 B1 | 2/2018 | Heit |
| 9,950,164 B2 | 4/2018 | Lipani |
| 10,143,850 B2 | 12/2018 | Cowan et al. |
| 10,307,585 B2 | 1/2019 | Boggs et al. |
| 10,493,275 B2 | 2/2019 | Alataris |
| 10,232,180 B2 | 3/2019 | Kramer et al. |
| 10,238,872 B2 | 3/2019 | Pivonka et al. |
| 10,328,256 B1 | 6/2019 | Gliner |
| 10,342,977 B2 | 7/2019 | Raghunathan |
| 10,369,366 B2 | 8/2019 | Oron et al. |
| 10,426,959 B2 | 10/2019 | Boggs, II |
| 10,583,284 B2 | 3/2020 | Peters et al. |
| 10,668,285 B2 | 6/2020 | Boggs, II |
| 10,799,701 B2 | 10/2020 | Lee |
| 11,534,611 B2 | 12/2022 | Baldoni et al. |
| 11,986,657 B2 | 5/2024 | Lee |
| 2003/0018367 A1 | 1/2003 | DiLorenzo |
| 2003/0055464 A1 | 3/2003 | Darvish et al. |
| 2004/0015204 A1 | 1/2004 | Whitehurst |
| 2004/0039425 A1 | 2/2004 | Greenwood-Van Meerveld |
| 2005/0240241 A1 | 10/2005 | Yun et al. |
| 2008/0033511 A1 | 2/2008 | Dobak et al. |
| 2008/0077192 A1 | 3/2008 | Harry et al. |
| 2009/0076565 A1 | 3/2009 | Surwit |
| 2009/0204173 A1 | 8/2009 | Fang et al. |
| 2010/0274314 A1 | 10/2010 | Alataris |
| 2010/0274326 A1 | 10/2010 | Chitre et al. |
| 2011/0071593 A1 | 3/2011 | Parker et al. |
| 2012/0303098 A1 | 11/2012 | Perryman |
| 2013/0204324 A1 | 8/2013 | Thacker et al. |
| 2013/0274846 A1 | 10/2013 | Lad et al. |
| 2014/0316484 A1 | 10/2014 | Edgerton et al. |
| 2015/0073510 A1 | 3/2015 | Perryman |
| 2016/0030408 A1 | 2/2016 | Levin |
| 2016/0121109 A1 | 5/2016 | Edgerton |
| 2016/0177298 A1 | 6/2016 | Green |
| 2016/0213918 A1 | 7/2016 | Howard et al. |
| 2016/0256683 A1 | 9/2016 | Butera et al. |
| 2017/0095667 A1 | 4/2017 | Yakovlev |
| 2017/0274212 A1 | 9/2017 | Kramer et al. |
| 2017/0354831 A1 | 12/2017 | Burnett et al. |
| 2018/0272132 A1 | 1/2018 | Subbaroyan et al. |
| 2018/0028824 A1 | 2/2018 | Pivonka et al. |
| 2018/0085580 A1 | 3/2018 | Perez et al. |
| 2018/0256906 A1 | 9/2018 | Pivonka et al. |
| 2018/0318585 A1 | 11/2018 | Pfeifer |
| 2018/0345020 A1 | 12/2018 | Ironi et al. |
| 2018/0361154 A1 | 12/2018 | Levin |
| 2019/0001139 A1 | 1/2019 | Mishra et al. |
| 2019/0046795 A1 | 2/2019 | Cakmak |
| 2019/0151652 A1 | 5/2019 | Boggs, II |
| 2019/0232062 A1 | 8/2019 | Falowski |
| 2019/0269913 A1 | 9/2019 | Pivonka et al. |
| 2019/0321641 A1 | 10/2019 | Baldoni et al. |
| 2019/0336776 A1 | 11/2019 | Cowan et al. |
| 2019/0351235 A1 | 11/2019 | Leuthardt et al. |
| 2019/0374776 A1 | 12/2019 | Mishra et al. |
| 2020/0030606 A1 | 1/2020 | Boggs, II |
| 2020/0046973 A1 | 2/2020 | Simon et al. |
| 2020/0046981 A1 | 2/2020 | Kramer et al. |
| 2020/0108251 A1 | 4/2020 | Raghunathan |
| 2020/0139138 A1 | 5/2020 | Sit et al. |
| 2020/0324113 A1 | 10/2020 | Fisher |
| 2020/0353253 A1 | 11/2020 | Subbaroyan et al. |
| 2021/0275812 A1 | 9/2021 | Subbaroyan et al. |
| 2021/0330981 A1 | 10/2021 | Mishra et al. |
| 2023/0191133 A1 | 6/2023 | Baldoni et al. |
| 2023/0248973 A1 | 8/2023 | Subbaroyan et al. |

FOREIGN PATENT DOCUMENTS

| | | |
|---|---|---|
| KR | 10-2021-0050493 | 6/2013 |
| WO | WO-2013036880 | 3/2013 |
| WO | WO-2014146082 | 9/2014 |
| WO | WO-2017044904 | 3/2017 |
| WO | WO-2017142948 | 8/2017 |
| WO | WO-2017146658 | 8/2017 |
| WO | WO-2018125538 | 7/2018 |
| WO | WO-2020051484 | 3/2020 |

OTHER PUBLICATIONS

Al-Kaisy et al., "The Use of 10-Kilohertz Spinal Cord Stimulation in Cohort of Patients with Chronic Neuropathic Limb Pain Refractory to Medical Management," Neuromodulation: Technology at the Neural Interface, Feb. 2014, 7 pages.

Cata et al., "Spinal cord stimulation relieves chemotherapy-induced pain: A Clinical Case Report," Journal of Pain and Symptom Management—10.1016/j.jpainsymman, vol. 27, No. 1, Jan. 2004, 7 pages.

CISION PRWeb, "Seattle Pain Relief Now Offering Groundbreaking Treatments for Diabetic and Peripheral Neuropathy," http://www.prweb.com/releases/seattle-pain-center/diabeticneuropathydoctor/prweb12492970.htm Jul. 25, 2022, 3 pages.

Daousi C et al., "Electrical spinal cord stimulation in the long-term treatment of chronic painful diabetic neuropathy" Diabet Med. 2005;22(4):6 pages.

De Vos et al., "Burst spinal cord stimulation evaluated in patients with failed back surgery syndrome and painful diabetic neuropathy" Neuromodulation. 2014;17(2):152-9.

De Vos et al., Effect and safety of spinal cord stimulation for treatment of chronic pain caused by diabetic neuropathy. J Diabetes Complications. 2009;23(1): 6 pages.

De Vos et al., "Spinal cord stimulation in patients with painful diabetic neuropathy: a multicentre randomized clinical trial" Pain. 2014;155(11):2426-31.

De Vos et al., "Spinal cord stimulation in patients with painful diabetic neuropathy: a multicentre randomized clinical trial," Pain. 2014;155(11):.6 pages.

Duarte et al., "Quality of life increases in patients with painful diabetic neuropathy following treatment with spinal cord stimulation" Qual Life Res. 2016;25(7):7 pages.

Eisenberg et al., "Quantitative Sensory Testing for Spinal Cord Stimulation in Patients With Chronic Neuropathic Pain. Pain Practice" 2006;6(3):5 pages.

Eldabe et al. "Retrospective Case Series on the Treatment of Painful Diabetic Peripheral Neuropathy With Dorsal Root Ganglion Stimulation." Neuromodulation. 2018;21(8): 6 pages.

Koetsier et al., "Effectiveness of dorsal root ganglion stimulation and dorsal column spinal cord stimulation in a model of experimental painful diabetic polyneuropathy," CNS Neurosci Ther. 2019;25(3): 8 pages.

Koetsier et al., "Mechanism of dorsal root ganglion stimulation for pain relief in painful diabetic polyneuropathy is not dependent on GABA release in the dorsal horn of the spinal cord" CNS Neurosci Ther. 2020;26(1): 8 pages.

Kumar et al., "Spinal cord stimulation for chronic pain in peripheral neuropathy" Surg Neurol. 1996;46(4):7 pages.

McDonnell et al., "Treatment of pain secondary to diabetic peripheral neuropathy (DPN) wit the precisions spinal cord stimulation (SCS) system: a case series," European Journal of Pain 11(S1), 2007, 1 page.

(56) References Cited

OTHER PUBLICATIONS

National Institute of Neurological Disorders and Stroke (NINDS), "Paresthesia," https://www.ninds.gov/Disorders/All-Disorders/Paresthesia-Information-Page#disorders-r3>, 2014, 2 pages.

Pluijms et al. "Increased contact heat evoked potential stimulation latencies in responders to spinal cord stimulation for painful diabetic polyneuropathy," Neuromodulation. 2015;18(2) 7 pages.

Pluijms et al., "Pain relief and quality-of-life improvement after spinal cord stimulation in painful diabetic polyneuropathy: a pilot study" British Journal of Anaesthesia. 2012;109(4):7 pages.

Pluijms et al., "The effect of spinal cord stimulation frequency in experimental painful diabetic polyneuropathy" Eur J Pain. 2013;17(9):9 pages.

Seattle Pain Relief Now Helping Diabetic Neuropathy Patients Restore Sensation with Spinal Cord Stimulation, PRWeb Online Visibility from Vocus, https://www.prweb.com/releases/diabetic-neuopathy/seattle-tacoma-wa/prweb13080906.htm, 2015, 2 pages.

Seattle Pain Relief Video: "What is a Spinal Cord Stimulator," https://www.painmanagement-seattle.com/spinal-cord-stimulator.html 2016, 5 pages.

Slangen et al., "Spinal cord stimulation and pain relief in painful diabetic peripheral neuropathy: a prospective two-center randomized controlled trial" Diabetes Care. 2014;37(11):3016-24.

Tesfaye et al., "Electrical Spinal-Cord Stimulation for Painful Diabetic Peripheral Neuropathy," The Lancet, vol. 348, Dec. 1996, 4 pages.

Van Beek et al. "Sustained Treatment Effect of Spinal Cord Stimulation in Painful Diabetic Peripheral Neuropathy: 24-Month Follow-up of a Prospective Two-Center Randomized Controlled Trial. Diabetes Care" 2015;38(9):3 pages.

Van Beek et al., "Long-Term Spinal Cord Stimulation Alleviates Mechanical Hypersensitivity and Increases Peripheral Cutaneous Blood Perfusion in Experimental Painful Diabetic Polyneuropathy" Neuromodulation. 2018;21(5):8 pages.

Van Beek et al., "Severity of Neuropathy Is Associated With Long-term Spinal Cord Stimulation Outcome in Painful Diabetic Peripheral Neuropathy: Five-Year Follow-up of a Prospective Two-Center Clinical Trial" Diabetes Care. 2018;41(1): 7 pages.

Van Beek et al., "Spinal Cord Stimulation in Experimental Chronic Painful Diabetic Polyneuropathy: Delayed Effect of High-Frequency Stimulation," European Journal of Pain, Oct. 2016, 9 pages.

YouTube Video: Spinal Cord Stimulator Implants Help Diabetic Peripheral Neuropathy (602) 507-6550, https://www.youtube.com/watch?v=EYao-SfPOwo, Jul. 23, 2012, 3 pages.

Mayo Clinic, "Diabetic Neuropathy," https://www.mayoclinic.org/diseases-conditions/diabetic-neuropathy/symptoms-causes/syc-20371580, 1998, 5 pages.

Petersen et al., "Durability of High-Frequency 10-KHz Spinal Cord Stimulation for Patients with Painful Diabetic Neuropathy Refractory to Conventional Treatments: 12-Month Results from a Randomized Controlled Trial," Diabetes Care, https://doi.org/10.2337/dc21-1813, 2021, 4 pages.

Strand et al., titled "Neuromodulation in the Treatment of Painful Diabetic Neuropathy: A Review of Evidence for Spinal Cord Stimulation", Journal of Diabetes Science and Technology vol. 16(2):332-340, 337, 2022.

Feldman et al., "Diabetic Neuropathy," Nature Reviews—Disease Primers, 2019, 18 pages.

Slangen et al., "Sustained effect of spinal cord" stimulation on pain and quality of life in painful diabetic peripheral neuropathy British Journal of Anaesthesia, 2013;111(6):1030-1031, 2 pages.

Raghu et al., ". Invasive Electrical Neuromodulation for the Treatment of Painful Diabetic Neuropathy: Systematic Review and Meta-Analysis," Neuromodulation: Technology at the Neural Interface, 2020, 9 pages.

Galan et al., "10-KHz spinal cord stimulation treatment for painful diabetic neuropathy: results from post-hoc analysis of the SENZA-PPN study," Pain Management., 10(5), 2020, 10 pages.

Petersen et al., "Effect of High-frequency (10-KHz) Spinal Cord Stimulation in Patients With Painful Diabetic Neuropathy: A Randomized Clinical Trial. JAMA Neurology," 78(6), 2021, 12 pages.

Petersen et al., "High-Frequency 10-KHz Spinal Cord Stimulation Improves Health-Related Quality of Life in Patients with Refractory Painful Diabetic Neuropathy: 12-Month Results From a Randomized Controlled Trial," Mayo Clinic Proceedings., 6(4), 2022, 14 pages.

Sloan et al., "The treatment of painful diabetic neuropathy," Current Diabetes Reviews, Bentham Science, 2021, 55 pages.

Duarte et al., "Spinal cord stimulation for the management of painful diabetic neuropathy: a systematic review and meta-analysis of individual patient and aggregate data," Pain, 2021, 9 pages.

Duarte R, et al. Systematic review and network met-analysis of neurostimulation for painful Diabetic Neuropathy, Diabetes Care, vol. 46, 2023, 2 pages.

International Search Report and Written Opinion for International Patent Application No. PCT/US2023/069368, Applicant: Nevro Corp., mailed Oct. 17, 2023, 12 pages.

Karamian et al., "The role of electrical stimulation for rehabilitation and regeneration after spinal cord injury," Journal of Orthopaedics and Traumatology, Jan. 6, 2022, 18 pages.

|  | Demography | Diagnoses/ Etiology | Time since injury | Location of injury | Medical History | Pre-Treatment ||||| Post-Treatment |||
|---|---|---|---|---|---|---|---|---|---|---|---|---|---|
|  |  |  |  |  |  | Symptoms | Pain Location | VAS | Lead Location | Best Program | Symptoms | VAS | Comments |
| Patient 1 | 62, F | SCI injury – Fell off ski lift | 33 years | T8 | Wheelchair bound, ITP for spasticity, multilevel thoracic laminectomy w/ SC detethering | Paraplegia, dystonia, spasms ("dancing legs"), able to sit for 10-15 mins | Low back, chest wall | Low back: 8 upper back: 9, right UL: 8 and bilateral leg: 9 | T8-T11 | Cascade on top lead | Spasms stopped; Able to sit for several hours | Low back: 3 (perc trial); Upper back, bilateral leg: 0, R UL: 2 | Perc leads in gutter; 2nd trial w paddle leads; Pain relief in upper back, leg and right UL with MA program (Lower C6: 1-3 and Lower T5: 9-11) w/ 20s on for each area |
| Patient 2 | 32, F | Cervical SCI w incomplete quadriplegia; dislocated ribs in car accident |  |  | Multi-level cervical fusion; Blocks for dislocated ribs | Thoracic pain; uses crutch/cane; Spasticity | Upper back | 7 | C1-T10 | Mid T2 | Improved movement ("tone"), walk smoothly; funct'l capacity in paralyzed leg, reduction in rib pain; improved spasticity... | 2 |  |
| Patient 3 | 32, F | Migraine; Partial SCI w "significant damage at T9/10" | 8 years |  |  | Paraplegic | Migraine; Low back pain | 8 |  | C3, 1.4 mA (Duty cycling) | Mild sensation in legs (slight itching); pin prick sensation which went away when stim went off; Flex both ankles in dorsi- and plantar-flexion; stand | 5 and at last follow-up (Trial) | HF10 trialed for head pain and migraine; Failed other neuromod therapies; Migraine and LBP under control |
| Patient 4 |  |  |  |  |  | pain in foot for 22 years; could not feel pin prick at foot; no Babinski | Foot |  | Top of T8 to top of T12 | Bipole between contacts 14 and 15 | Reduced pain in foot; could feel pin prick at foot; had normal Babinski reflex |  |  |
| Patient 5 |  |  |  |  |  | No sensation in feet | n/a |  |  |  | Sensation in feet |  |  |

*FIG. 4*

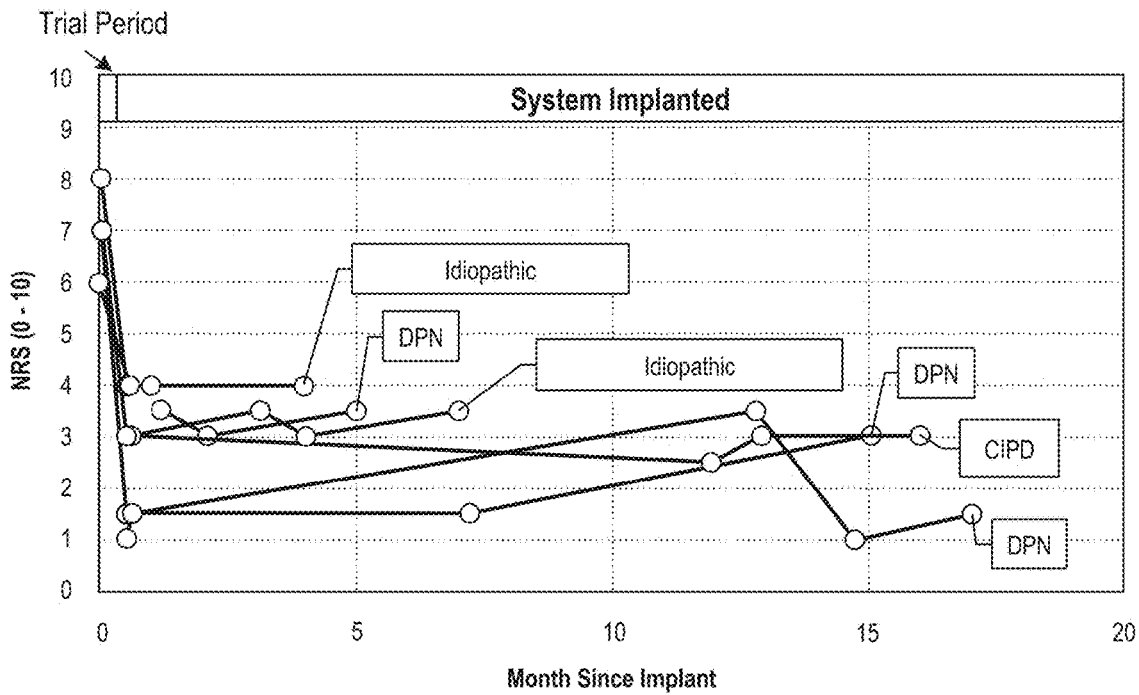

*FIG. 5A*

| Sex | Age | Patient Diagnosis | Medication Adjustment During Follow-up | Sensation Level Relative to Baseline |
|---|---|---|---|---|
| M | 66 | Idiopathic | reduced | no change |
| M | 63 | Idiopathic | reduced | improved, reported 25% |
| M | 34 | DPN | reduced | not reported |
| F | 57 | DPN | Completely off Medication | improved, reported 60% |
| M | 70 | DPN | NA (no meds at baseline) | improved |
| F | 70 | CIPD | no change* | NA |

* medications were initially reduced, later adjusted up due to new pain in the upper body

NEUROSTIMULATION FOR TREATING SENSORY DEFICITS, AND ASSOCIATED SYSTEMS AND METHODS

CROSS-REFERENCE TO RELATED APPLICATION(S)

The present application is a continuation of U.S. Patent Application Ser. No. 18/344,579, filed on Jun. 29, 2023, now issued as U.S. Pat. No. 11,986,657, which claims priority to U.S. Provisional Patent Application No. 63/357,798, filed Jul. 1, 2022, both of which are incorporated by reference herein in its entirety.

TECHNICAL FIELD

The present disclosure is directed generally to electrical stimulation for treating sensory deficits in patients, and associated systems and methods.

BACKGROUND

An estimated 20 million people in the United States have some form of peripheral neuropathy, a condition that develops as a result of damage to the peripheral nervous system ("PNS"). The PNS is a vast communications network that connects the central nervous system ("CNS") to the limbs and organs, essentially serving as a communication relay going back and forth between the brain and spinal cord with the rest of the body. Damage to the PNS interferes with this communication pathway, and symptoms can range from numbness or tingling, to pricking sensations or muscle weakness. Peripheral neuropathy has been conventionally treated with medication, injection therapy, physical therapy, surgery, and light. More recently, diabetic peripheral neuropathy has been treated by applying a surface electrical stimulation at a specified frequency to the muscles and nerves. Most treatments are designed to treat the underlying cause of the neuropathy, but in many cases, the cause of the neuropathy is unknown or, even if the cause has been identified, a specific treatment may not exist. Accordingly, there is a need for systems and methods for treating peripheral neuropathy.

BRIEF DESCRIPTION OF THE DRAWINGS

FIG. 4 is a table showing selected clinical data gathered from Applicant's clinical study showing treatment of sensory deficit with high frequency spinal cord stimulation, in accordance with embodiments of the present technology.

FIGS. 5A-5C illustrate clinical results for patients treated for peripheral polyneuropathy with high frequency stimulation in accordance with embodiments of the present technology.

DETAILED DESCRIPTION

1.0 Introduction

Figure 1:
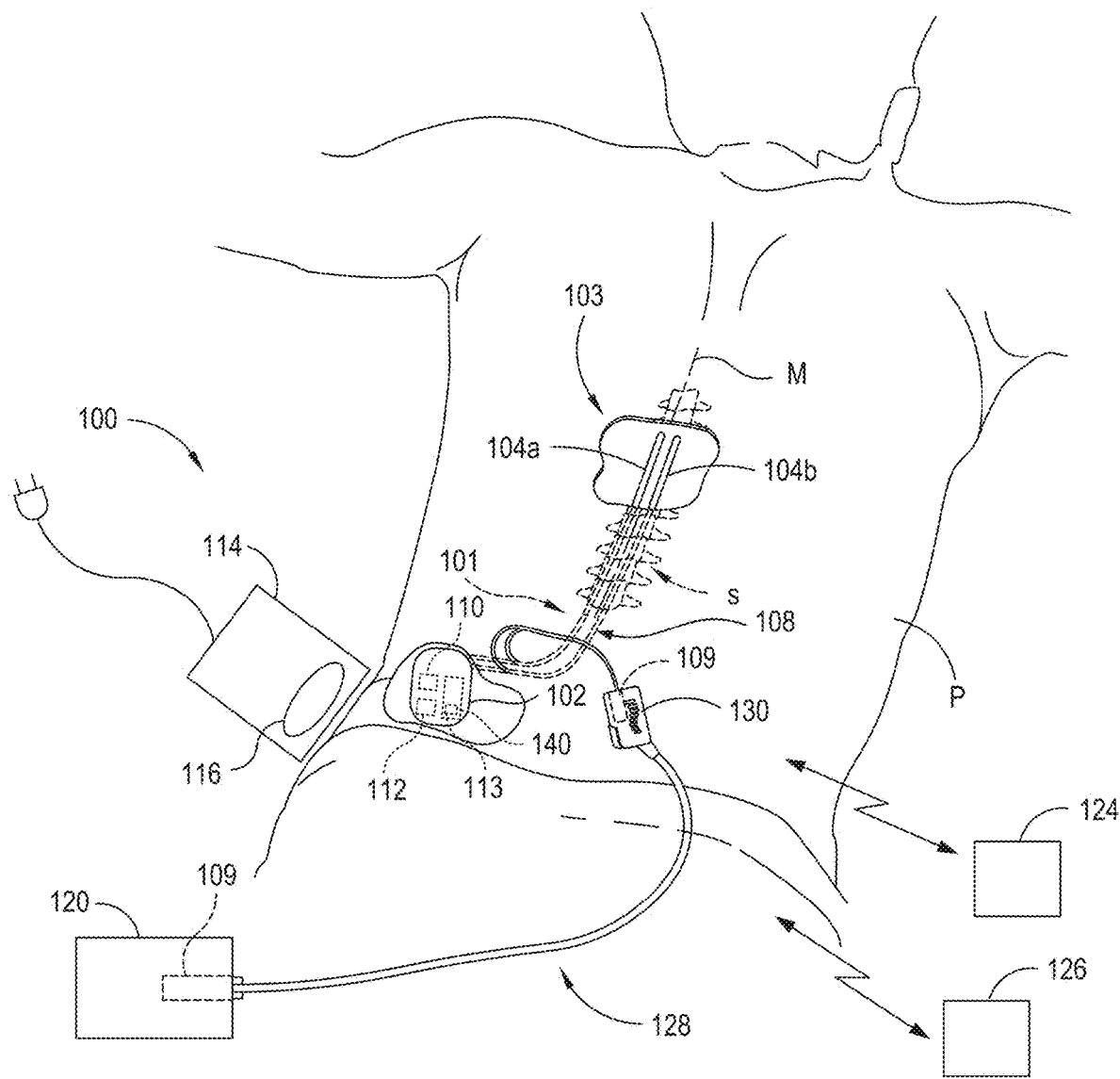
FIG. 1 is a partially schematic illustration of an implantable spinal cord modulation system positioned at the spine to deliver therapeutic signals in accordance with embodiments of the present technology.

The present technology is directed generally to systems and methods for treating peripheral neuropathy, peripheral polyneuropathy (PPN), diabetic neuropathy, painful diabetic neuropathy (PDN), dysesthesia, sensory deficits, motor deficits, and/or spinal cord injury using high frequency electrical stimulation. In particular, the systems and methods of the present technology may at least partially restore sensory loss in patients suffering from peripheral neuropathy and/or other indications. In one embodiment, the present technology includes improving the patient's somatosensory function by delivering an electrical signal, having a frequency of from 200 Hz to 100 kHz, to the patient's spinal cord via at least one implantable signal delivery device.

Definitions of selected terms are provided under heading 1.0 ("Definitions"). General aspects of the anatomical and physiological environment in which the disclosed technology operates are described below under heading 2.0 ("Introduction"). Representative treatment systems and associated methods, are described under heading 3.0 ("Representative Treatment Systems and Associated Methods") with reference to FIGS. 1-3. Representative clinical data generated from the use of Applicant's treatment systems and methods disclosed herein are described under heading 4.0 ("Representative Clinical Data") with reference to FIG. 4-5C. Representative mechanisms of action are discussed under heading 5.0 ("Representative Mechanisms of Action") with reference to FIGS. 6A-8B. Representative signal delivery parameters are discussed under heading 6.0 ("Representative Signal Delivery Parameters"). Representative examples are described under Heading 7.0 ("Representative Examples"). The foregoing headings are provided for organizational purposes only. Features defined and/or described above under any of the foregoing headings may be combined with and/or applied to features described under any of the other headings, in accordance with embodiments of the present technology.

2.0 Definitions

As used herein, the terms "high frequency" and "HF" refer to a frequency of from about 1.2 kHz to about 100 kHz, or from about 1.5 kHz to about 100 kHz, or from about 2 kHz to about 50 kHz, or from about 3 kHz to about 20 kHz, or from about 3 kHz to about 15 kHz, or from about 5 kHz to about 15 kHz, or from about 3 kHz to about 10 KHz, or 1 kHz, 2 KHz, 3 kHz, 4 kHz, 5 kHz, 10 KHz, 15 kHz, 20 kHz, 50 kHz, or 100 kHz, unless otherwise stated. Unless otherwise stated, the term "about" refers to values within 10% of the stated value. As used herein, "low frequency" or "LF" refers to a frequency less than 1.2 kHz or less than 1 kHz.

As used herein, "peripheral neuropathy" refers to damage to or disease affecting one or more peripheral nerves or groups of peripheral nerves. Peripheral neuropathy may refer to nerve damage or disease in one nerve or area of the body (mononeuropathy), multiple nerves or multiple areas of the body (polyneuropathy), and/or in the same place on both sides of the body (symmetric neuropathy). Representative systems and methods in accordance with embodiments of the present technology are configured to treat all types of peripheral neuropathy, irrespective of whether it is inherited or acquired. Inherited causes include Charcot-Marie Tooth, Kennedy's disease (X-linked bilbospinal muscular atrophy), Van Allen's Syndrome (hereditary amyloid neuropathy), Refsum's disease, Tangier disease, and others. Causes of acquired peripheral neuropathy addressed by the systems and methods of the present technology include nerve compression, entrapment or laceration (e.g., crutches, ulnar neuropathy, thoracic outlet syndrome, meralgia paresthetica, Morton's metatarsalgia); metabolic (diabetes mellitus, hypothyroidism) and autoimmune disorders (lupus, rheumatoid arthritis, Guillain-Barre Syndrome, Miller Fisher Syndrome); kidney disease, liver disease, toxin-induced (alcohol, tobacco, asbestos, arsenic, lead, mercury); cancer (e.g., malignant lymphoma, lung cancer, etc.); viral or bacterial infections (HIV, Lyme disease, leprosy, poliomyelitis); medication-induced (e.g., chemotherapy, etc.); trauma; repetition (carpal tunnel syndrome, cubital tunnel syndrome); and vitamin deficiency (especially vitamin B).

As used herein, "treat" or "treatment" with reference to peripheral neuropathy includes preventing, ameliorating, suppressing, or alleviating one or more of the symptoms of abnormal sensory responses caused by peripheral neuropathy. In some cases, the treatment protocols of the present technology result in the reactivation of the nerve (e.g., restoring the ability of the nerve to depolarize and conduct signals).

As used herein, the terms "sensory deficit," "sensory loss," "abnormal sensory response," "abnormal sensory function," etc. refer to all symptoms caused by disease and/or damage to the peripheral nerves (large and/or small fiber) of the somatosensory system, such as numbness, abnormal (e.g., decreased, or increased) responsiveness to light touch, pain, thermal sensation, and vibratory sensation, impaired joint position sense, impaired balance, and decreased muscle strength. The terms "somatosensory" refers generally to sensations (such as pressure, pain, or warmth) that can occur anywhere in the body, as opposed to a particular organ-specific sense, such as sight or smell. The foregoing terms also include "dysesthesia", an unpleasant and/or abnormal sense of touch, which in turn can include sensations of burning, wetness, itching, electric shock, and/or pins and needles, and which can affect any tissue, including but not limited to the mouth, skin, scalp and/or legs. The therapy signals described herein may address somatosensory dysfunction by restoring or at least partially restoring sensation that was lost in association with the somatosensory dysfunction. When addressing or treating somatosensory dysfunction using high-frequency therapy signals in accordance with the present technology, the therapy signals may also have an effect on the patient's perception of pain—but in a different manner than that associated with existing techniques for treating chronic pain via high frequency signals. In particular, existing high frequency therapy signal regimens for addressing chronic pain are generally designed to reduce or eliminate pain (e.g., chronic, neuropathic pain). By contrast, when high frequency therapy signals are administered in accordance with the present technology to address or treat somatosensory dysfunction, they may operate to improve, restore or at least partly restore the patient's ability to detect and/or perceive pain (e.g., by restoring sensation in the patient and, as a result, enabling the patient to perceive painful inputs). Now, if the patient also suffers from chronic pain, the high frequency therapy signal can be administered in a manner that also addresses (reduces) chronic pain, in addition to addressing somatosensory deficits.

3.0 Representative Treatment Systems and Associated Methods

FIG. 1 schematically illustrates a representative treatment system 100 for treating peripheral neuropathy and/or other sensory deficits, positioned relative to the general anatomy of a patient's spinal column S. The treatment system 100 can include a signal delivery system 101 having a signal generator 102 (e.g., a pulse generator) and a signal delivery device 103 comprising one or more signal delivery elements 104 (referred to individually as first and second signal delivery elements 104a, 104b, respectively). The signal generator 102 can be connected directly to the signal delivery element(s) 104, or it can be coupled to the signal delivery element(s) 104 via a signal link 108 (e.g., an extension). In some embodiments, the signal generator 102 may be implanted subcutaneously within a patient P. As shown in FIG. 1, the signal delivery element(s) 104 is configured to be positioned at or proximate to the spinal cord to apply a high frequency electrical signal to the spinal cord (e.g., to the white matter and/or glial cells of the spinal cord). Without being bound by theory, it is believed that glial cells are present in large concentrations within both white and grey matter, and that high frequency modulation at or proximate to the white and grey matter can affect electrically deficient glial cells. However, the therapies described herein may provide effective treatment via other mechanisms of action.

In representative embodiments, the signal delivery device 103 includes the first and second signal delivery elements 104a, 104b, each of which comprises a flexible, isodiametric lead or lead body that carries features or structures, for delivering an electrical signal to the treatment site after implantation. As used herein, the terms "lead" and "lead body" include any of a number of suitable substrates and/or support members that carry structures, for providing therapy signals to the patient. For example, the lead body can include one or more electrodes or electrical contacts that direct electrical signals into the patient's tissue, such as to directly affect a cellular membrane. In some embodiments, the signal delivery device 103 and/or signal delivery elements 104 can include devices other than a lead body (e.g., a paddle) that also direct electrical signals and/or other types of signals to the patient. Additionally, although FIG. 1 shows an embodiment utilizing two signal delivery elements 104, in some embodiments the signal delivery system 101 and/or signal delivery device 103 can include more or fewer signal delivery elements (e.g., one signal delivery element, 104 three signal delivery elements 104, four signal delivery elements 104, etc.), each configured to apply electrical signals at different locations and/or coordinate signal delivery to deliver a combined signal to the same (or generally the same) anatomical location.

As shown in FIG. 1, the first signal delivery element 104a can be implanted on one side of the spinal cord midline M, and the second signal delivery element 104b can be implanted on the other side of the spinal cord midline M. For example, the first and second signal delivery elements 104a, 104b shown in FIG. 1 may be positioned just off the spinal cord midline M (e.g., about 1 mm offset) in opposing lateral directions so that the first and second signal delivery elements 104a, 104 are spaced apart from each other by about 2 mm. In some embodiments, the first and second signal delivery elements 104a, 104b may be implanted at a vertebral level ranging from, for example, about T8 to about T12. In some embodiments, one or more signal delivery devices can be implanted at other vertebral levels, depending, for example, on the specific indication for which the patient is being treated.

The signal generator 102 can transmit signals (e.g., electrical therapy signals) to the signal delivery element 104 that up-regulate (e.g., stimulate or excite) and/or down-regulate (e.g., block or suppress) target nerves (e.g., local vagal nerves). As used herein, and unless otherwise noted, to "modulate," "stimulate," or provide "modulation" or "stimulation" to the target nerves refers generally to having either type of the foregoing effects on the target nerves. The signal generator 102 can include a machine-readable (e.g., computer-readable) medium containing instructions for generating and transmitting suitable therapy signals. The signal generator 102 and/or other elements of the treatment system 100 can include one or more processors 110, memories 112 and/or input/output devices 140. Accordingly, the process of providing electrical signals, detecting physiological parameters of the patient, adjusting the modulation signal, and/or executing other associated functions can be performed by computer-executable instructions contained by computer-readable media located at the signal generator 102 and/or other system components. The signal generator 102 can include multiple portions, elements, and/or subsystems (e.g., for directing signals in accordance with multiple signal delivery parameters) housed in a single housing, as shown in FIG. 1, or in multiple housings.

The signal delivery system 101 can include one or more sensing elements 113 for detecting one or more physiological parameters of the patient before, during, and/or after the application of electrical therapy signals. In some embodiments, one or more of the sensing elements 113 can be carried by the signal generator 102, the signal delivery element 104, and/or other implanted components of the system 101. In some embodiments, the sensing element 113 can be an extracorporeal or implantable device separate from the signal generator 102 and/or signal delivery element 104. Representative sensing elements 113 include one or more of: a subcutaneous sensor, a temperature sensor, an impedance sensor, a chemical sensor, a biosensor, an electrochemical sensor, a hemodynamic sensor, an optical sensor and/or other suitable sensing devices. Physiological parameters detected by the sensing element(s) 113 include neurotransmitter concentration, local impedance, current, and/or voltage levels, and/or any correlates and/or derivatives of the foregoing parameters (e.g., raw data values, including voltages and/or other directly measured values).

The signal generator 102 can also receive and respond to one or more input signals received from one or more sources. The input signals can direct or influence the manner in which the therapy and/or process instructions are selected, executed, updated, and/or otherwise performed. The input signals can be received from one or more sensors (input devices, 140 (e.g., the sensor 113) shown schematically in FIG. 1 for purposes of illustration) that are carried by the signal generator 102 and/or distributed outside the signal generator 102 (e.g., at other patient locations) while still communicating with the signal generator 102. The sensor 113 and/or other input devices 140 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference.

In some embodiments, the signal generator 102 can obtain power to generate the therapy signals from an external power source 114. The external power source 114 can transmit power to the implanted signal generator 102 using electromagnetic induction (e.g., RF signals). For example, the external power source 114 can include an external coil 116 that communicates with a corresponding internal coil (not shown) within the implantable signal generator 102. The external power source 114 can be portable for ease of use.

In some embodiments, the signal generator 102 can obtain the power to generate therapy signals from an internal power source, in addition to or in lieu of the external power source 114. For example, the implanted signal generator 102 can include a non-rechargeable battery or a rechargeable battery to provide such power. When the internal power source includes a rechargeable battery, the external power source 114 can be used to recharge the battery. The external power source 114 can in turn be recharged from a suitable power source (e.g., conventional wall power).

During at least some procedures, an external generator 120 (e.g., a trial stimulator or modulator) can be coupled to the signal delivery element 104 during an initial procedure, prior to implanting the signal generator 102. For example, a practitioner (e.g., a physician and/or a company representative) can use the external generator 120 to provide therapy signals and vary the modulation parameters provided to the signal delivery elements 104 in real time, and select optimal or particularly efficacious parameters. These parameters can include the location from which the electrical signals are emitted, as well as the characteristics of the electrical signals provided to the signal delivery elements 104. In some embodiments, input is collected via the external generator 120 and can be used by the clinician to help determine what parameters to vary. In a typical process, the practitioner uses a cable assembly 128 to temporarily connect the external generator 120 to the signal delivery element 104. The practitioner can test the efficacy of the signal delivery elements 104 in an initial position. The practitioner can then disconnect the cable assembly 128 (e.g., at a connector 130), reposition the signal delivery elements 104, and reapply the electrical signal. This process can be performed iteratively until the practitioner obtains the desired signal parameters and/or position for the signal delivery element 104. Optionally, the practitioner can move the partially implanted signal delivery element 104 without disconnecting the cable assembly 128. Furthermore, in some embodiments, the iterative process of repositioning the signal delivery elements 104 and/or varying the therapy parameters may not be performed. Instead, the practitioner can place signal delivery element(s) 104 at an approximate anatomical location, and then select which electrodes or contacts deliver the therapy signal, as a way of varying the location to which the therapy signal is directed, without repositioning the signal delivery element(s).

After the signal delivery elements 104 are implanted, the patient P can receive therapy via signals generated by the external generator 120, generally for a limited period of time. During this time, the patient wears the cable assembly 128 and the external generator outside the body. Assuming the trial therapy is effective or shows the promise of being effective, the practitioner then replaces the external generator 120 with the implanted signal generator 102, and programs the signal generator 102 with therapy programs selected based on the experience gained during the trial period. Optionally, the practitioner can also replace the signal delivery elements 104. The signal delivery parameters provided by the signal generator 102 can still be updated after the signal generator 102 is implanted, via a wireless physician's programmer 124 (e.g., a physician's remote) and/or a wireless patient programmer 126 (e.g., a patient remote). Generally, the patient P has control over fewer parameters than does the practitioner. For example, the capability of the patient programmer 126 may be limited to starting and/or stopping the signal generator 102, and/or adjusting the signal amplitude. The patient programmer 126 may be configured to accept pain relief input as well as other variables, such as medication use.

The signal generator 102, the lead extension, the external programmer 120 and/or the connector 130 can each include a receiving element 109. Accordingly, the receiving elements 109 can be implantable elements (implantable within the patient), or the receiving elements 109 can be integral with an external patient treatment element, device or component (e.g., the external generator 120 and/or the connector 130). The receiving elements 109 can be configured to facilitate a simple coupling and decoupling procedure between the signal delivery elements 104, the lead extension, the signal generator 102, the external generator 120, and/or the connector 130. The receiving elements 109 can be at least generally similar in structure and function to those described in U.S. Patent Application Publication No. 2011/0071593, incorporated by reference herein.

Figure 2:
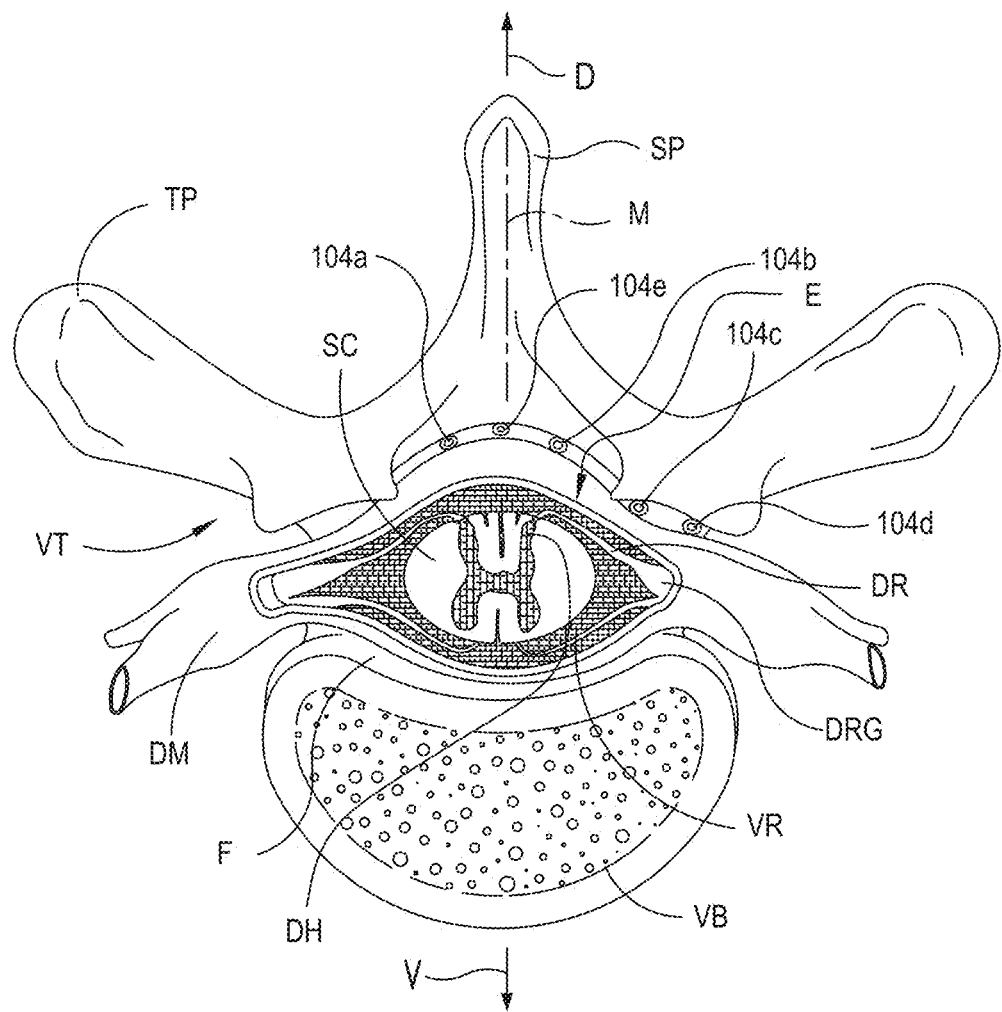
FIGS. 2-3 are partially schematic, cross-sectional illustrations of a patient's spine, illustrating representative locations for implanted lead bodies in accordance with embodiments of the present technology.
Figure 3:
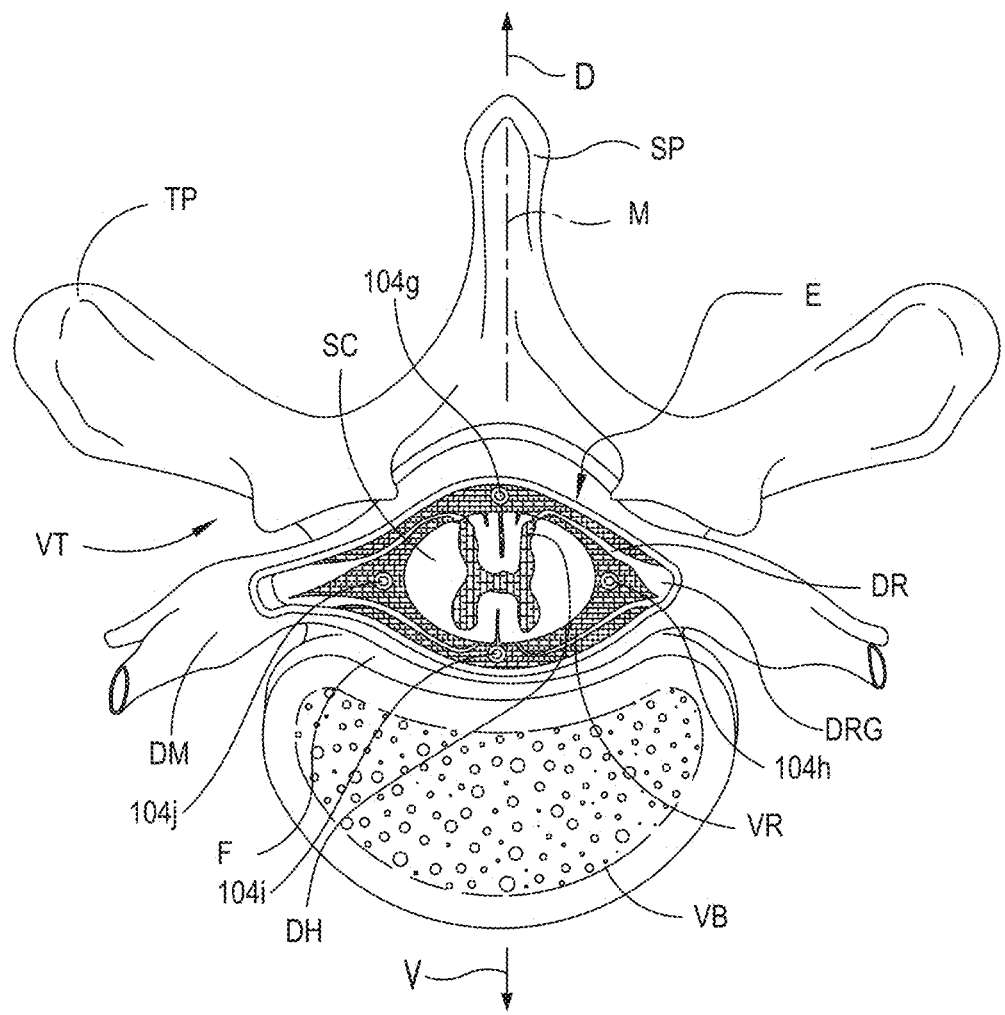

FIG. 2 is a cross-sectional illustration of a spinal cord SC and an adjacent vertebra VT (based generally on information from Crossman and Neary, "Neuroanatomy," 1995 (published by Churchill Livingstone)), along with multiple signal delivery elements 104 (shown as signal delivery elements 104a-104f) implanted at representative locations. For purposes of illustration, multiple signal delivery elements 104 are shown in FIG. 2 implanted in a single patient. In actual use, any given patient will likely receive fewer than all the signal delivery elements 104 shown in FIG. 2.

As shown in FIG. 2, the spinal cord SC is situated within a vertebral foramen F, between a ventrally located ventral body VB and a dorsally located transverse process TP and spinous process SP. Arrows V and D identify the ventral and dorsal directions, respectively. The spinal cord SC itself is located within the dura mater DM, which also surrounds portions of the nerves exiting the spinal cord SC, including the ventral roots VR, dorsal roots DR and dorsal root ganglia DRG. The dorsal roots DR enter the spinal cord SC at the dorsal root entry zone E, and communicate with dorsal horn neurons located at the dorsal horn DH. In one embodiment, the first and second signal delivery elements 104a, 104b are positioned just off the spinal cord midline M (e.g., about 1 mm offset) in opposing lateral directions so that the two signal delivery elements 104a, 104b are spaced apart from each other by about 2 mm. In other embodiments, a lead or pairs of leads can be positioned at other epidural locations, e.g., toward the outer edge of the dorsal root entry zone E as shown by a third signal delivery element 104c, or at the dorsal root ganglia DRG, as shown by a fourth signal delivery element 104d, or approximately at the spinal cord midline M, as shown by a fifth signal delivery element 104e, or near the ventral roots, as shown by a sixth signal delivery element 104f. In some embodiments, the leads are positioned near the exit of the ventral roots may be advantageous to modify ventral motor pools located in the gray matter. For example, modification of these ventral motor pools may treat spasticity, motor disorders and/or other disorders arising from the ventral motor pools.

In some embodiments, it may be advantageous to position one or more signal delivery elements 104 within the dura mater DM to target neural tissue and one or more glial cells present in the gray and white matter of the spinal cord SC. For example, as shown in the cross-sectional view of a spinal cord SC in FIG. 3, in some embodiments a seventh signal delivery element 104g and an eighth signal delivery element 104i are positioned along the spinal cord midline M on the dorsal and ventral sides of the spinal cord SC, respectively. In some embodiments, one or more signal delivery elements 104 can be positioned at other locations. For example, in some embodiments a ninth signal delivery element 104h and a tenth signal delivery element 104j are positioned off the spinal cord midline M on opposing lateral sides of the spinal cord SC. High frequency signals applied to the tenth signal delivery element 104j may be especially effective at reducing sympathetic outflow. In some embodiments, high frequency signals applied to the tenth signal delivery element 104j may treat heart failure, hypertension, complex regional pain syndrome, peripheral vascular disease, and other diseases where elevated sympathetic tone is implicated. In some embodiments, one or more signal delivery elements 104 may be positioned in other suitable locations within the subdural space. Additionally, in some embodiments, a physician may position one or more signal delivery elements in the epidural space and one or more signal delivery elements in the subdural space. More generally any one of the foregoing signal delivery elements may be used alone or in combination with any other signal delivery element(s) 104, depending upon the patent indication(s).

4.0 Representative Clinical Data

FIG. 4 is a table 400 of selected clinical data gathered during Applicant's clinical study in which patients were implanted with one or more signal delivery elements in accordance with the devices, systems, and methods described in under heading 3.0 above. In particular, patients received electrical therapy signals at a frequency of 10 kHz, a pulse width of 30 microseconds, and an amplitude that ranged from about 0.5 mA to about 6 mA.

Table 400 includes the following acronyms/abbreviations:
SCI—spinal cord injury
ITP—Intrathecal pump
UL—Upper Limb
R—Right
SC—Spinal cord
MA program—Multi-area program
LBP—Low back pain As shown in the first row of the table 400, Patient 1 suffered from upper and lower back pain caused by a spinal cord injury at the eighth thoracic vertebrae. Patient 1 was paraplegic and presented with dystonia, spasms ("dancing legs"), and low back and chest wall pain. Before treatment, Patient 1 was able to sit comfortably for only 10-15 minutes. Based on Patient 1's pain location (lower and upper back), the lead electrodes were placed at or between the eighth and the eleventh thoracic vertebrae (T8-T11). After treatment, Patient 1's spasms were gone, and Patient 1 was able to sit for several hours.

As shown in the second row of table 400, Patient 2 suffered from thoracic pain caused by a cervical spinal cord injury. Patient 2 presented with a paralyzed leg, and spasticity. Before treatment, Patient 2 required a crutch for walking. Based on Patient 2's pain location (thoracic), the lead electrodes were placed at or near the vertical midpoint of the second thoracic vertebrae (T2). After treatment, Patient 2 had improved movement (i.e., improved "tone", and was able to walk smoothly), renewed functional capacity in the paralyzed leg, a reduction in thoracic pain, improvement in spasticity, and was able to transition from seated to standing positions that caused spasms or tone problems before treatment.

As shown in the third row of table 400, Patient 3 suffered from low back pain caused by a partial spinal cord injury with significant damage at the ninth and tenth thoracic vertebra (T9-T10). Patient 3 was paraplegic and also presented with migraines. Based on Patient 3's pain indications, the lead electrodes were placed at the third cervical vertebrae (C3). Patient 3's migraine and low back pain were successfully treated. After treatment, Patient 3's ability to sense slight itching was restored, and Patient 3 was able to sense pinpricks in the legs as long as the high frequency stimulation was being delivered. Patient 3 was also able to flex both ankles in dorsi- and plantar-flexion, bend his legs at both knees, stand up and bear weight with support, and had spontaneous return of erectile function.

As shown in the fourth row of table 400, Patient 4 presented with foot pain from small fiber neuropathy (peripheral neuropathy) and could not sense a pin-prick sensation in that foot. Patient 4 presented with Babinski reflex, severe and constant muscle spasms in the back, constant burning sensation at the skin, and stabbing pain in the low- and mid-back. Based on Patient 4's pain indication, the lead electrodes were placed to span from the superior aspect of the eighth thoracic vertebrae (T8) to the superior aspect of the twelfth thoracic vertebrae (T12). After treatment, Patient 4 experienced restored pin-prick sensations in the foot, the Babinski reflex disappeared and the patient experienced reduced pain in the foot.

As shown in the fifth row of table 400, Patient 5 presented with no pin prick sensation. After a trial period, Patient 5 had restored pin prick sensation in the feet. Sensation was maintained at follow-up visits. Ten additional patients (not represented in table 400) also presented with no pin prick sensation, and also had their pinprick sensation restored following treatment in accordance with the foregoing parameters (frequency of 10 kHz, a pulse width of 30 microseconds, and an amplitude that ranged from about 0.5 mA to about 6 mA). These cases, as well as others discussed herein, are representative of patients recovering pain-based sensory responses via a high frequency electrical therapy.

An additional patient, not represented in table 400, was a paraplegic SCI patient, with a lesion at T11 and with neuropathic lower back pain. His T10-L2 vertebral bodies were fused as a result of injury. Following several failed (more conservative) therapies, he received a high frequency therapy regimen in accordance with the foregoing parameters via a single lead positioned epidurally between the T10-L1 vertebral bodies. In general, leads for high frequency therapy are placed at T8-T11 for back pain, but in this case, the lead could not be advanced (in a rostral direction) past mid-T10. The patient had a dural puncture during the procedure and the resulting headache prevented accurate reporting of pain scores for the first two days of the trial period. However, by the third day, the patient reported significant back pain relief. At the end of the seven day trial period, the patient reported 80% pain relief and was able to voluntarily move his leg for the first time in 15 years. Sensation to touch and pin prick were restored from the L1-S1 dermatomes. His neurological status improved from spastic paralysis at baseline to non-spastic weakness. In addition, for the last three days of the trial, the patient had regained micturition control and had stopped self-catheterizing.

The electrical therapy treatment methods of the present technology may be used with other therapies (e.g., conventional therapies) for peripheral neuropathy treatment. Such therapies include, but not limited to: corticosteroids; IV immunoglobulins; plasma exchange or plasmapheresis; immunosuppressive agents; surgery; mechanical aids; avoiding toxins including alcohol; aldose reductase inhibitors; fish oil; gamma-linolenic acid; gangliosides; lipoic acid; myoinositol; nerve growth factor; protein kinase C inhibitors; pyridoxine; ruboxistaurin mesylate; thiamine; vitamin B12; pain relievers including codeine; anti-seizure medications including gabapentin, topiramate, pregabalin, carbamazepine, and phenytoin; topical anesthetics such as lidocaine; tricyclic antidepressant medications such as amitriptyline and nortriptyline; selective serotonin and norepinephrine reuptake inhibitors such as duloxetine; and mexiletine. The agents may also include, for example, dopamine uptake inhibitors, monoamine oxidase inhibitors, norepinephrine uptake inhibitors, dopamine agonists, acetocholinesterase inhibitors, catechol O-methyltransferase inhibitors, anticholinergic agents, antioxidants, as well as synaptic and axonal enhancing medications. Additionally, it has been observed that HF therapy can reduce the need for supplemental medications. For example, in a randomized controlled trial of HF therapy for low back and leg pain, concomitant morphine-equivalent medication use and dosage were significantly reduced. Thus, in the context of the present technology, those agents used as primary, supplemental, or adjuvant treatments can be reduced, bringing the benefit of both reduced side-effects and patient compliance burden, when HF therapy is successfully applied.

Further Clinical Results

The following sections described further clinical results obtained by treating patients with therapy signals at frequencies in the range of 1.5 kHz to 100 KHz.

(a) Peripheral Polyneuropathy

Figure 5C:
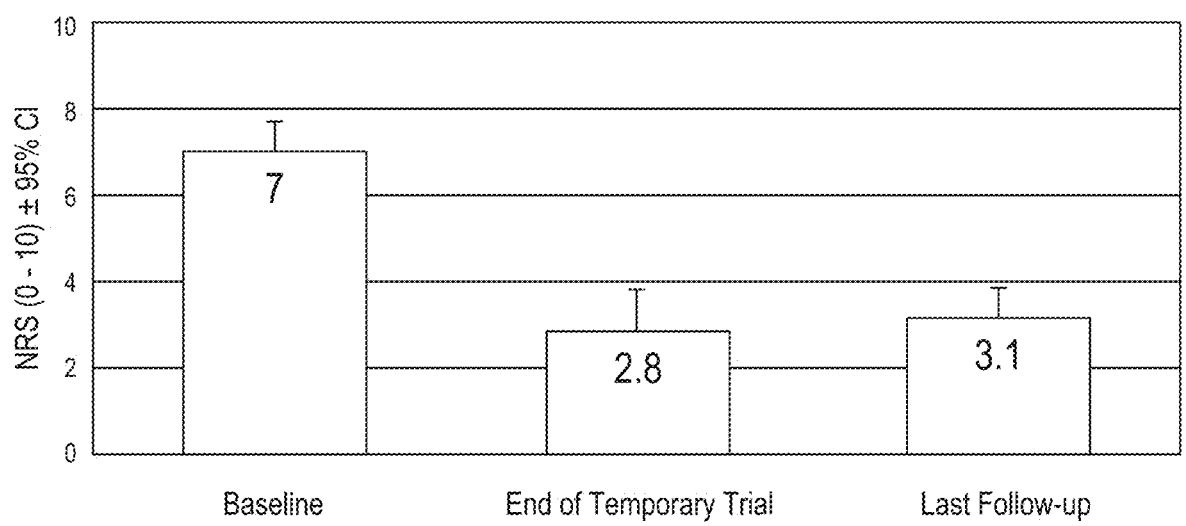

FIGS. 5A-5C illustrate data obtained from six peripheral polyneuropathy patients, all presenting with bilateral lower extremity pain. Each of the patients was treated with a therapy signal at 10 kHz, applied to the patient at the T8-T11 vertebral level. The signal had a pulse width of 30 microseconds, and an amplitude that varied from patient to patient. As shown in FIG. 5A, three patients were diagnosed with diabetic peripheral neuropathy, two patients with idiopathic peripheral neuropathy, and one patient with chronic inflammatory demyelinating polyneuropathy. Five of the six patients experienced at least a 50% reduction in pain during an approximately one week trial period, and all were implanted with a pulse generator and signal delivery device.

As shown in FIG. 5B, four of the five patients who received medication prior to receiving treatment via the 10 KHz therapy signal had their medication reduced or eliminated. As is also shown in FIG. 5B, several of the patients also reported an improvement in sensation level relative to baseline.

FIG. 5C illustrates the pain scores of the patients at baseline, at the end of the temporary trial, and as of a subsequent follow-up (10.7 months, plus or minus 6 months). These data indicate that the patients received a significant reduction in pain, which was sustained over a significant period after the trial period.

Anecdotally, an additional diabetic patient (not included in the data shown in FIGS. 5A-5C) suffered a significant amount of pain in his lower legs, which were ulcerated. He was near to receiving an amputation of his leg, prior to receiving electrical signal therapy at 10 KHz via an implanted stimulation device in accordance with the foregoing parameters. After stimulation for a period of two months, the patient's pain was reduced, the patient's wounds were healing, the color returned to the patient's legs, and the patient was walking, whereas previously the patient had been in a wheelchair.

(b) Post-Stroke Pain

In still a further example, patients were treated for central post-stroke pain (CPSP). CPSP refers to chronic neuropathic pain resulting from lesions of the central somatosensory nervous system, particularly the spinothalamocortical pathway. The prevalence of CPSP is 1-12% in stroke patients, and symptom onset usually occurs within six months. Most patients complain of burning, allodynia, and hyperalgesia. CPSP is typically pharmacoresistant, and therapeutic options for refractory cases are limited.

An 85-year-old male with a prior history of hypertension, pre-diabetes, and stroke presented for management of right lower extremity (RLE) pain. One year earlier, he had presented with a new left-sided weakness. Following a stroke diagnosis, he underwent intensive rehabilitation and had near complete resolution of left hemibody weakness. However, six months later, he began to experience new RLE pain. Workup for re-stroke was negative. The patient's pain was constant and burning, with an average intensity of 8 on a numerical rating scale of 0-10 for pain assessment, and associated with allodynia and hyperalgesia. He received no benefit from amitriptyline, physical therapy or a right lumbar sympathetic block.

The patient received spinal cord stimulation at 10 kHz, with a signal delivery device spanning the T8-T11 vertebral bodies. The patient received a successful trial and then underwent permanent implantation. At an 8-week follow-up, he reported greater than 80% pain relief, with an average pain score of 2 and significant improvement in his quality of life. Based at least upon this patient's outcome, it is believed that stimulation in accordance with the foregoing parameters can prove effective for medically refractory CPSP.

(c) Foot Drop

In another example, two patients presented with both chronic low back pain, and bilateral foot drop following complications from prior spinal surgeries. Patient 1, a 62-year-old woman, experienced persistent foot drop for 13 years, ambulating with aides. Electromyogram (EMG) tests revealed mild sensorimotor axonal polyneuropathy, with demyelinating features. The patient was affected by chronic neurogenic deficits affecting vertebral levels L4-L5 and S1 bilaterally, with active denervation affecting the L5 root on the right side. The patient had been prescribed with analgesics for control of pain at a level of 8 out of 10 on the numerical rating scale, which induced unpleasant side effects.

Patient 2 was a 45-year-old male who suffered from acute paraplegia complications following spinal surgery. His neurological deficit gradually improved, but his back pain and bilateral lower extremity weakness remained, with this right side worse, resulting in an ankle-foot orthosis. Arachnoiditis was evident at the L4-L5 level, with significant clumping of the nerve roots at this level. The patient received strong analgesics for his back pain, which was at a level of 5⁸⁄₁₀ on the numerical rating scale.

After receiving stimulation at 10 kHz during a trial, both patients proceeded to a permanent implant at a vertebral level of T8-T11. By three months post-implant, both patients no longer required orthotics, and began weaning opioids. At six months, Patient 1's foot drop had completely resolved, with a return of sensation and no pain. At nine months, Patient 1 had weaned off opioids completely, reporting significant improvements in function without aides, and was able to drive a car. Patient 2 no longer used opioids at six months post-implant, and reported almost complete resolution of his foot drop. In addition, Patient 2 reported an average pain score of one on a scale of ten, improved walking, and the ability to ride a bicycle.

It is expected that dorsally positioned electrodes can provide the foregoing motor benefits. For example, dorsal white matter tracts feed into spinal grey matter circuits to inhibit/facilitate reflex and motor coordination. In pathologic states, or in the absence of descending control, these circuits may become dysfunctional, e.g., spastic, tonic, and/or dis-coordinated. HF therapy can 'normalize' these circuits via grey matter and/or glial effects, to restore patient function and activities of daily living.

(d) Dysesthesia

In still further example, several patients suffering from dysesthesia were treated with spinal cord stimulation at a frequency of 10 kHz, a pulse width of 30 microseconds, and a current amplitude that varied from patient to patient. Prior to treatment, the patients were diagnosed with peripheral polyneuropathy and/or painful diabetic neuropathy. Some patients experienced the inability to feel the bottoms of their feet, which created balance and gait issues, and some patients experienced foot numbness and tingling. After 6-7 days of receiving therapy at 10 kHz, the foot numbness and tingling disappeared, and the patients experienced an improvement in gait.

The foregoing gait and sensory improvements can be particularly significant for patients suffering from diabetes, because when such patients can walk, they are better able to control their blood sugar. Patients are also better able to avoid falls and fractures, which are additional issues associated with diabetic patients.

Based on the foregoing, it is expected that stimulation in accordance with the foregoing parameters can be used to address lower limb pain, foot and ankle pain, other types of focal, neuropathic pain, and/or dysesthesia. These results are expected to be achieved with spinal cord stimulation delivered at 10 kHz or other high frequency values, to the dorsal structures of the patient's spinal cord. This is contrary to conventional techniques, which may require that stimulation be applied to the dorsal root ganglion.

In addition, based on the foregoing results, stimulation in accordance with the parameters disclosed herein can produce benefits in addition to, or in lieu of, pain reduction. Such benefits involve restoration of sensory and/or motor functions.

Further Indications

The discussion above describes representative therapies in the context of treatment for spinal cord injury, peripheral neuropathy and other indications. In some embodiments, the therapy can be administered to patients with peripheral polyneuropathy indications. More generally, the therapy can be applied to patients with other indications, other indications that are associated with sensory loss, and/or motor deficits. As an example, in at least some cases, the observed sensory improvement is correlated (e.g., other indications directly or indirectly) with motor improvement. Accordingly, the foregoing techniques can be used to facilitate sensory and/or motor function recovery. In particular, at least one patient (Patient 2 described above with reference to FIG. 4) experienced a reduction in spasticity, as well as other motor-related improvements, in addition to a reduction in pain.

It is expected that, in at least some embodiments, the foregoing therapies can be used to address sensory deficit, and/or motor deficit, and/or spinal cord injury, in combination with treating pain. In some embodiments, the foregoing therapies can be used to address sensory deficit, and/or motor deficit, and/or spinal cord injury, independent of whether or not the therapy is also used to treat pain. In at least some embodiments, the target location of the therapy signal may be different, depending on whether the therapy is used to address pain, or one or more of a sensory deficit, motor deficit, or spinal cord injury. For example, in at least some cases, it was found that therapy delivered to treat segmental pain also produced an improvement in sensory response, but at a location rostral or caudal to the segmental pain indication.

It is also believed that sensory deficit can be reversed when treating polyneuropathy, without moving the therapy treatment site, and that foot pain can be addressed with a more generalized treatment location (e.g., T8-T12), as opposed to a specific location (such as the DRG at L5 or S1). More generally, it is believed that the therapy can be applied to the spinal cord instead of the DRG (which is where at least some conventional low frequency treatments are applied). Advantages of applying the therapy signal to the spinal cord rather than the DRG include (a) a lower incidence of adverse events/safety concerns, and/or (b) a broader electric field spread that may have additional pain and/or other benefits, whereas DRG stimulation is typically very focal. In addition, implanting the signal delivery device at the spinal cord may be simpler and easier to "standardize" than implanting the signal delivery device at the DRG.

Several embodiments of the present technology were described above in the context of therapy signals applied to the patient's spinal cord region. In other embodiments, the therapy signal may be applied to other locations, e.g., peripheral locations.

Without being bound by theory, it is possible that treating motor and sensory deficits may result from different mechanisms of action. For example, it may be that hyperpolarization of the lamina I/II neurons explains the resolution of spastic/dystonic (motor) symptoms (e.g., caused by a barrage of spontaneous firing), and the therapies described above hyperpolarize those cells resulting a reduced/normalized neuronal activity level. In the foregoing example, the hyperpolarization of lamina I/II neurons that reduces motor symptoms/normalizes neuronal activity may include hyperpolarization of hyperexcitable I/III projection neurons. Because sensory deficit may be due to lack of input from neurons, the ability to address sensory deficit as well as motor symptoms via the same therapy signal may be an indication that different mechanisms of action are responsible for each result. For example, the beneficial effect on motor symptoms may result from a reversal of inhibition or hyperpolarization. Alternatively, the normalization of the sensory input may be the cause of a reduced motor dysfunction. In other words, the sensorimotor reflex may be returned to normal when the sensory neuron returns to normal. Potential mechanisms of action underlying the treatment of sensory deficits are described below under Section 5.0.

5.0 Representative Mechanisms of Action

As described above, the present technology includes systems and methods for treating neuropathies. In many of the embodiments described above, the neuropathy treatment restores sensation that was lost in association with the neuropathy, in addition to or in lieu of treating pain associated with the neuropathy. For example, as set forth above, the present technology provides spinal cord stimulation therapies that can at least partially restore sensation in patients suffering from, e.g., diabetic neuropathy.

Figure 6A:
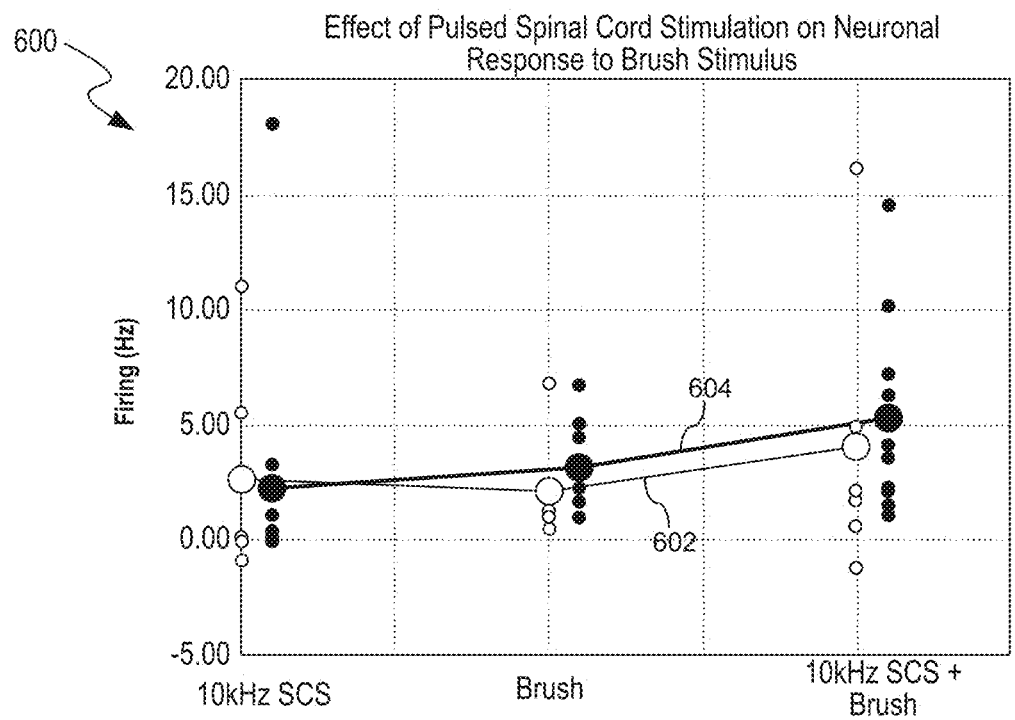
FIGS. 6A and 6B illustrate a neural response to a brush stimulus under various conditions and in accordance with embodiments of the present technology.

The Applicant of the present application has performed several animal studies related to the mechanisms of action underlying the sensory restoration induced via spinal cord stimulation. FIG. 6A is a graph 600 illustrating a change in neural activity recorded in rats subjected to various conditions/stimuli. In FIG. 6A, the line 602 represents a change in neural activity relative to a baseline (e.g., spontaneous) neural activity for adapting (e.g., excitatory) neurons, and the line 604 represents a change in neural activity relative to a baseline (e.g., spontaneous) neural activity for non-adapting (e.g., inhibitory) neurons. The data was collected under three conditions, labeled on the x-axis: (1) during application of 10 kHz spinal cord stimulation, (2) during application of a brush stimulus, and (3) during simultaneous application of both 10 KHz spinal cord stimulation and the brush stimulus. For condition 1, the 10 KHz spinal cord stimulation was applied for a period of one second, and the neuronal response was measured for the one second period. The neuronal response was then averaged over the one second period and compared to the baseline neuronal activity (represented as 0.00 on the y-axis). For condition (2), the brush stimulus was applied manually by an operator for one second, and the neuronal response was measured for that one second period. The neuronal response to the brush stimulus was then averaged over the one second period and compared to the baseline neuronal firing rate. For condition (3), the brush stimulus was applied manually by an operator for one second and at the same time that a one second period of 10 kHz spinal cord stimulation was delivered. The neuronal response to the combination of the brush stimulus and the 10 KHz spinal cord stimulation was measured for the one second period, and then compared to the baseline neuronal firing rate.

Figure 6B:
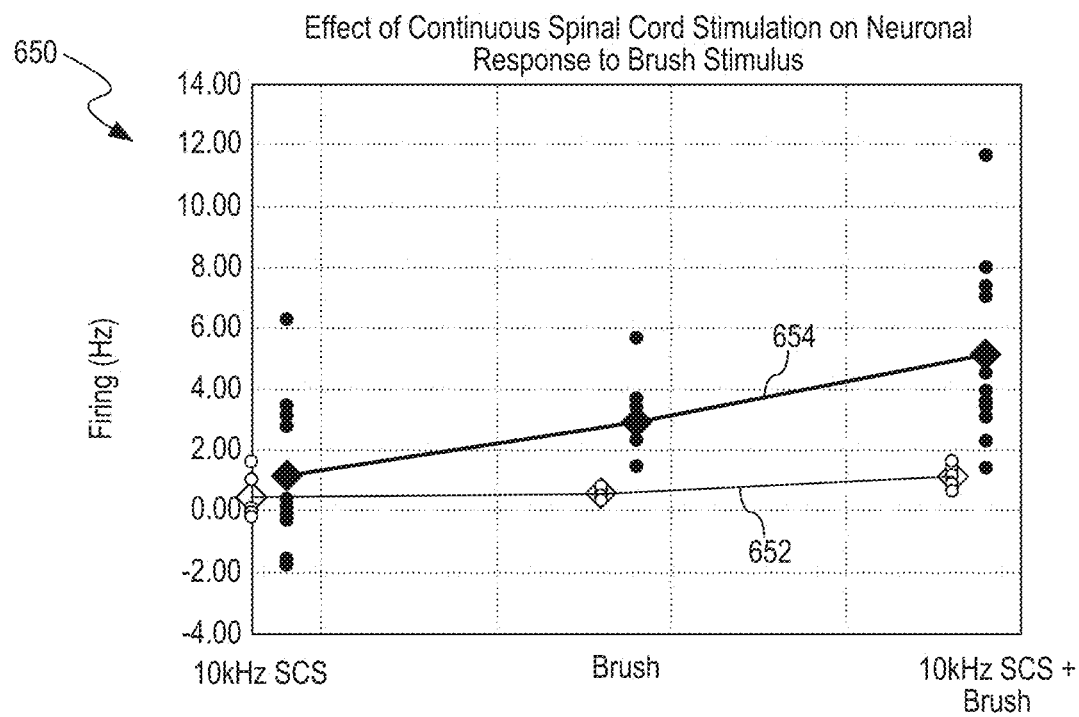

FIG. 6B is a graph 650 illustrating a change in neural activity recorded in the same rats used to collect the data shown in FIG. 6A, but in response to modified conditions/stimuli. In FIG. 6B, the line 652 represents a change in neural activity relative to a baseline (e.g., spontaneous) neural activity for adapting (e.g., excitatory) neurons, and the line 604 represents a change in neural activity relative to a baseline (e.g., spontaneous) neural activity for non-adapting (e.g., inhibitory) neurons. The data was collected under similar conditions as shown in FIG. 6A, also labeled on the x-axis: (1) during application of 10 KHz spinal cord stimulation, (2) during application of a brush stimulus, and (3) during simultaneous application of both 10 kHz spinal cord stimulation and the brush stimulus. Relative to the conditions described with respect to FIG. 6A, however, the data illustrated in FIG. 6B was collected during 20 seconds of continuous 10 kHz spinal cord stimulation. That is, for condition (1) (10 KHz SCS alone) and condition (3) (10 KHz SCS+Brush), 10 kHz stimulation was applied continuously for 20 seconds. For condition (3), a brush stimulus was applied five times over the 20 second period, with each brush stimuli having a duration of about one second. The neuronal response to each of the five brush stimuli was measured. The neuronal response to the five brush stimuli were then averaged and compared to the baseline neuronal activity (represented by 0.0 on the y-axis). Thus, the difference between FIGS. 6A and 6B is that, for conditions involving application of spinal cord stimulation in FIG. 6B, the rat had been receiving stimulation without cessation.

Referring first to FIG. 6A, both adapting neurons (line 602) and non-adapting neurons (line 604) behaved similarly to the various conditions/stimuli. For example, adapting neurons demonstrated a slightly increased firing rate in response to 10 KHz SCS (e.g., about 2.5-3 Hz greater than baseline), in response to brush stimulus (e.g., about 2.0-2.5 Hz greater than baseline), and in response to a combination of 10 KHz SCS and brush stimulus (e.g., about 4.5-5 Hz greater than baseline). Non-adapting neurons also demonstrated a slightly increased firing rate in response to 10 KHz SCS (e.g., about 2.5-3 Hz greater than baseline), in response to brush stimulus (e.g., about 3.0-3.5 Hz greater than baseline), and in response to a combination of 10 KHz SCS and brush stimulus (e.g., about 5.0-5.5 Hz greater than baseline). For both adapting and non-adapting neurons, the neural activity in response to the combined application of 10 KHz SCS and brush was greater than the neural activity in response to either 10 KHz SCS or brush stimulus by itself. That is, the 10 KHz SCS at least partially increased the neural response of both adapting and non-adapting neurons to brush stimulus.

Referring next to FIG. 6B, the adapting neurons (line 652) and non-adapting neurons (line 654) responded differently to the modified conditions/stimuli. For example, adapting neurons demonstrated a very slight increase in response to 10 KHz SCS (e.g., about 0.5-1.0 Hz greater than baseline), in response to brush stimulus alone (e.g., about 0.5-1.0 Hz greater than baseline), and in response to a combination of 10 KHz SCS and a brush stimulus (e.g., about 1.0-1.5 Hz greater than baseline). Without intending to be bound by theory, the relatively smaller increase in activity of adapting neurons seen in FIG. 6B as compared to FIG. 6A may be because in FIG. 6B the 10 KHz SCS was applied continuously for 20 seconds. Without intending to be bound by theory, the adapting neurons may have "adapted" to the 10 KHz stimulation and were therefore in a relatively quiescent period when the neural activity was measured. In contrast, the non-adapting neurons responded generally similarly in FIG. 6B as in FIG. 6A. In particular, non-adapting neurons had only a slight increase in neural activity in response to 10 KHz SCS (e.g., about 1.0-1.5 Hz greater than baseline), had a slightly greater increase in response to brush stimulus (e.g., about 2.5-3.0 Hz greater than baseline), and had the greatest increase in response to the combined application of 10 KHz SCS and brush stimulus (e.g., about 5.0-5.5 Hz greater than baseline). For both adapting and non-adapting neurons, the neural activity in response to the combined application of 10 kHz SCS and brush was greater than the neural activity in response to either 10 KHz SCS or brush stimulus by itself. That is, 10 KHz SCS at least partially increased the neural response of both adapting and non-adapting neurons to brush stimulus. However, relative to the data shown in FIG. 6A, FIG. 6B shows that continuous 10 KHz SCS increased the neural response of non-adapting neurons to a brush stimulus to a greater extent than the neural response of adapting neurons to the brush stimulus. For example, the neural response to brush went from about 3 Hz greater than baseline to about 5.5 Hz greater than baseline for non-adapting neurons, and only from about 0.75 Hz greater than baseline to about 1.25 Hz greater than baseline for adapting neurons. Accordingly, without intending to be bound by theory, it is expected that the application of 10 kHz spinal cord stimulation may preferentially increase the firing of non-adapting neurons to sensory inputs, described in greater detail below. Moreover, without intending to be bound by theory, even though the data in FIG. 6B was collected by applying 5 brush stimuli during 20 seconds of continuous stimulation, it is expected that a similar preferential increase in the firing of non-adapting neurons would be seen when a rat is subject to other periods of continuous stimulation (e.g., periods of greater than 20 seconds) and/or more or fewer brush stimuli during the continuous stimulation.

Figures 7A, 7B:
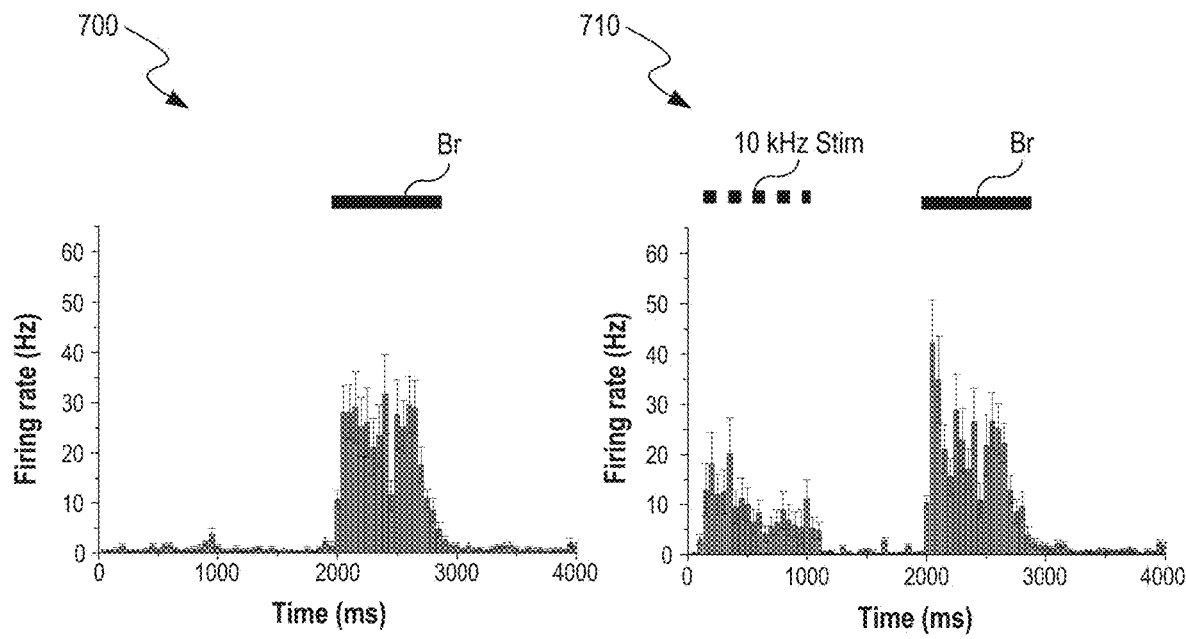
FIGS. 7A-7E illustrate a neural response of non-adapting neurons to a brush stimulus under various conditions and in accordance with embodiments of the present technology.
Figures 7C, 7D:
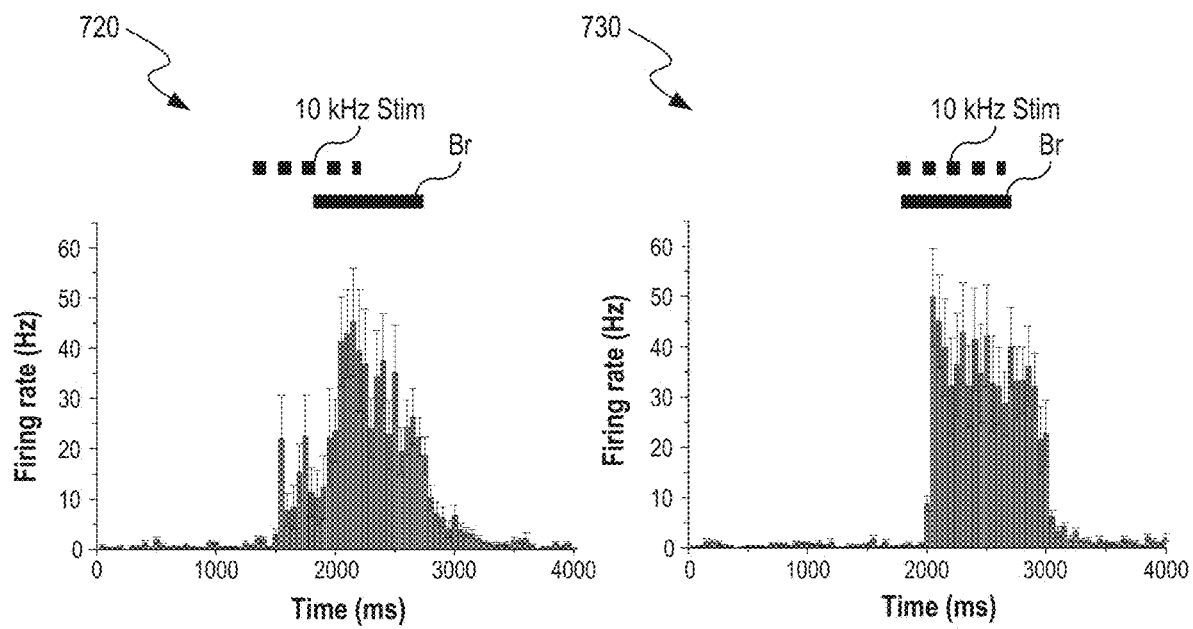

FIGS. 7A-7D are graphs showing the response of non-adapting neurons to various stimulus conditions. In particular, FIG. 7A is a graph 700 showing a neural response of non-adapting neurons to a one second brush stimulus. FIG. 7B is a graph 710 showing a neural response of non-adapting neurons to a one second pulse of 10 kHz stimulation and to a one second brush stimulus following the pulse of 10 kHz stimulation. FIG. 7C is a graph 720 showing a neural response of non-adapting neurons to a one second pulse of 10 KHz stimulation and to a one second brush stimulus that at least partially overlaps with the one second pulse of 10 kHz stimulation. FIG. 7D is a graph 730 showing a neural response of non-adapting neurons to a one second pulse of 10 KHz stimulation and to a one second brush stimulus that is applied at the same time as the one second pulse of 10 KHz stimulation. In each of FIGS. 7A-7D, the timing of the application of the brush stimulus is identified by a solid line labeled "Br", and the timing of the application of the 10 kHz spinal cord stimulation is identified by a dashed line labeled "10 KHz Stim."

Figure 7E:
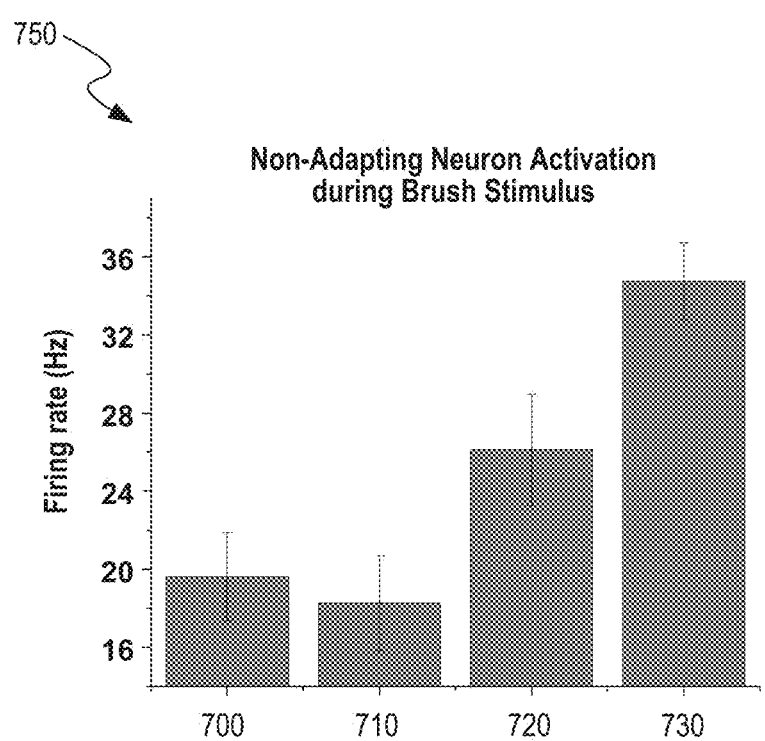

FIG. 7E is a graph 750 that illustrates the average firing rate recorded during the one second brush stimulus for each of graphs 700, 710, 720, and 730 (FIGS. 7A-7D). As best shown in FIG. 7E, the average firing rate of the non-adapting neurons in response to the one second brush stimulus (700) was about 20 Hz. The average firing rate of the non-adapting neurons in response to the one second brush stimulus applied after a one second pulse of 10 kHz stimulation (710) was about 18 Hz. The average firing rate of the non-adapting neurons in response to the brush stimulus that partially overlapped with the 10 kHz stimulation (720) was about 26 Hz. The average firing rate of the non-adapting neurons in response to the brush stimulus applied concurrently with the 10 kHz stimulation (730) was about 35 Hz. The neural activity recorded during application of the brush stimulus was therefore greater when the rat was subjected to spinal cord stimulation during the brush stimulus, consistent with the findings from FIGS. 6A and 6B. Moreover, without intending to be bound by theory, it is expected that the total neural response of the non-adapting neurons to the concurrent application of the brush stimulus and the 10 KHz stimulation (730) was approximately equal to the sum of the total neural response to the brush stimulus alone and the neural response to the 10 KHz stimulation alone. In other words, when 10 KHz stimulation is synchronized with a brush stimulus, the combined firing rate of non-adapting neurons may increase as an arithmetic summation of the neural response to brush stimulation alone and the neural response to 10 KHz stimulation alone. This suggests that the 10 KHz stimulation and the brush stimulus activate different neural pathways.

The data in FIGS. 6A-7E demonstrate one potential mechanism of action underlying the sensory restoration induced via spinal cord stimulation in patients with neuropathy-induced numbness. For example, and without intending to be bound by theory, the additive effect that spinal cord stimulation has on neural response to brush stimulus suggests that stimulation may activate inhibitory interneurons in pathways that are related to, but not entirely overlapping with, pathways that are activated by a brush stimulus. For example, the non-adapting neurons activated by spinal cord stimulation may include inhibitory interneurons that reduce or otherwise quiet abnormal sensory "noise" signals. That is, the spinal cord stimulation may reduce abnormal signaling from neurons that occurs in the absence of a sensory input. Such abnormal signaling may include abnormal signaling generated by peripheral neurons and/or by dorsal horn neurons. Thus, when the brush stimulus is applied, the correct afferent nerve fibers can be activated and transmit signals toward the sensory cortex in a normal manner, without being hidden or otherwise blocked by the abnormal sensory noise signals. As a result, the spinal cord stimulation may increase sensory discrimination in patients suffering from neuropathy-induced numbness, which may result in sensory restoration.

Figure 8A:
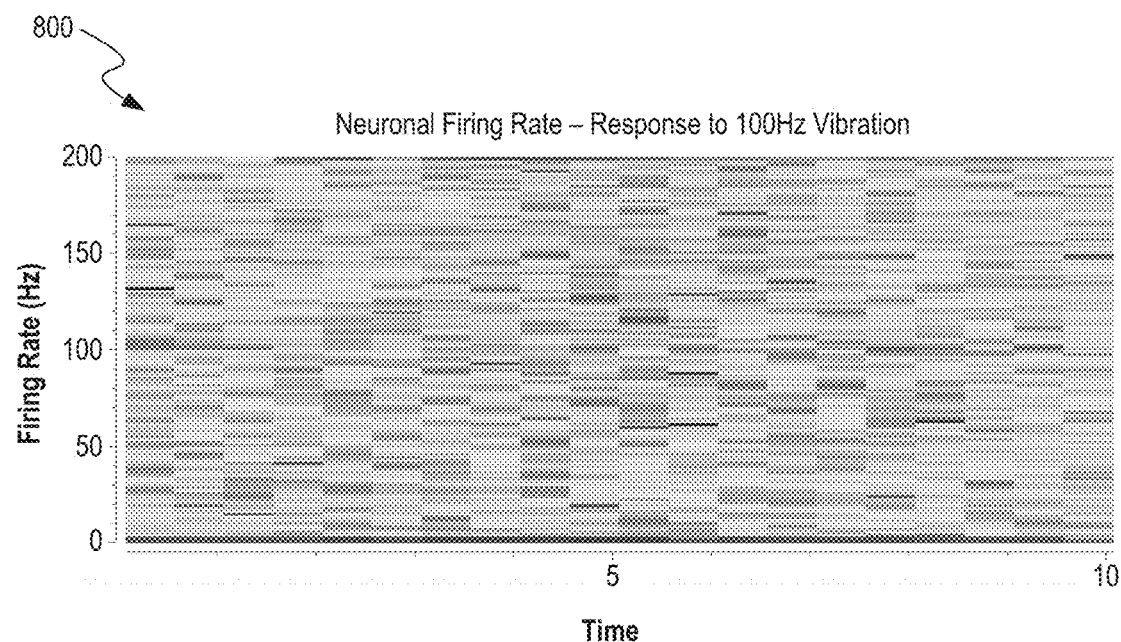
FIGS. 8A and 8B illustrate a neural response to a vibratory stimulus in the presence and absence of spinal cord stimulation in accordance with embodiments of the present technology.
Figure 8B:
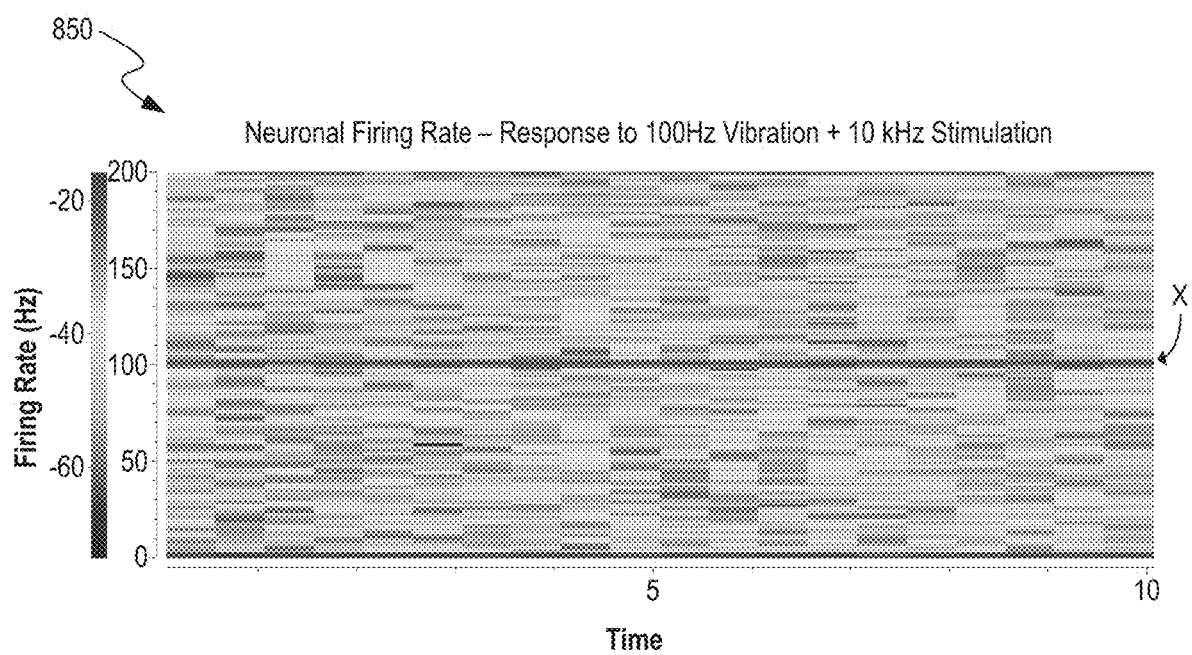

Spinal cord stimulation may also enable neurons to respond to stimuli that they would not respond to in the absence of spinal cord stimulation. FIG. 8A is a graph 800 illustrating a neural response to a 100 Hz vibrating sensory input applied to a rat's paw in the absence of spinal cord stimulation, and FIG. 8B is a graph 800 illustrating a neural response to the 100 Hz vibrating sensory input applied simultaneously with 10 kHz spinal cord stimulation. Referring first to FIG. 8A, the neurons did not substantially respond to the 100 Hz vibratory input in the absence of spinal cord stimulation. However, as shown in FIG. 8B, the neurons did respond to the 100 Hz vibratory input when the rate was subjected to 10 KHz spinal cord stimulation (the neural response is labeled with an arrow "X" in FIG. 8B). Thus, spinal cord stimulation enabled the neurons to respond to a sensory input (i.e., the 100 Hz vibratory input) that the neurons would not have otherwise been able to respond to. Without intending to be bound by theory, this suggests that sensory information that would not be transmitted to the sensory cortex (e.g., due to pathological conditions from disease) can be propagated to the sensory cortex in the presence of spinal cord stimulation. The data in FIGS. 8A and 8B therefore demonstrate another potential mechanism of action underlying the sensory restoration induced via spinal cord stimulation in patients with neuropathy-induced numbness.

Collectively, the data in FIGS. 6A-8B support that spinal cord stimulation can "boost" or otherwise increase transmission of meaningful sensory inputs through one or more mechanisms of action. In some embodiments, this may be similar to the concept of stochastic resonance, in which "noise-like information" (e.g., spinal cord stimulation, and in particular spinal cord stimulation with frequencies above 200 Hz, or above 1.2 kHz) increases a response of a system to an input signal (e.g., increases the response of sensory neurons to a meaningful sensory stimulus). Without intending to be bound by theory, this boosting of sensory information may be responsible for the sensory restoration induced via spinal cord stimulation in patients with neuropathy-induced numbness. Without intending to be bound by theory, this boosting effect may also be responsible for relief of other neuropathy-induced symptoms that can be obtained via spinal cord stimulation, such as relief from neuropathic pain and neuropathy-induced paresthesia.

As set forth above, in some embodiments the electrical signals described herein may increase the transmitted afferent neural activity induced by a sensory input (e.g., a touch, a pin prick, etc.). The increased transmission of this afferent neural activity may include increased activity of peripheral afferent fibers (e.g., at their central termini and/or branch points) and/or central afferent transmission neurons (e.g., projection neurons). The transmitted afferent neural activity can be increased by at least 25%, at least 50%, or at least 100% relative to the transmitted afferent neural activity induced by the same sensory input in the absence of the electrical signal.

As also set forth above, in some embodiments the electrical signals may activate different neurons than the sensory input. For example, the electrical signals can activate a first subset of neurons, and the sensory input can activate a second subset of neurons different than the first subset of neurons. In some embodiments, the first subset of neurons may include inhibitory interneurons, and the second subset of neurons may include afferent nerve fibers that ultimately transmit sensory information to the sensory cortex. The activation of the first subset of neurons may enhance signal transmission in (or otherwise normalize activity in) the second subset of neurons. In turn, the enhanced signal transmission in the second subset of neurons may improve the ability of a patient to perceive sensory inputs.

Although the data reported above in FIGS. 6A-8B was obtained using 10 KHz spinal cord stimulation, it is expected that a similar boosting effect may be obtained at other frequencies. For example, the boosting effect induced via spinal cord stimulation may be induced at frequencies referred to herein as high frequency, including frequencies in a frequency range of from about 1.2 kHz to about 100 kHz. In some embodiments, the boosting effect may be induced by frequencies greater than or less than the foregoing range of frequencies. For example, in some embodiments the boosting effect may be induced using frequencies between about 200 Hz and about 1.2 kHz. Representative electrical signals are described in greater detail below under the heading "Representative Signal Delivery Parameters."

6.0 Representative Signal Delivery Parameters

The therapy signals described above may be delivered in accordance with several suitable signal delivery parameters. For example, the signal frequency may be from about 1 Hz to about 100 kHz, or from about 50 Hz to about 100 kHz, or from about 200 Hz to about 100 kHz, or from about 500 Hz to about 100 kHz, or from about 1.2 kHz to about 100 kHz, or from about 1.5 kHz to about 100 kHz, or from about 2 kHz to about 50 kHz, or from about 3 kHz to about 20 kHz, or from about 3 kHz to about 15 kHz, or from about 5 kHz to about 15 kHz, or from about 3 kHz to about 10 KHz, or 1 kHz, 2 kHz, 3 kHz, 4 kHz, 5 kHz, 10 KHz, 15 kHz, 20 KHz, 50 KHz, or 100 kHz. In additional examples, the signal frequency may be from about 1 Hz to about 50 kHz, or from about 50 Hz to about 25 kHz, or from about 200 Hz to about 20 kHz, or from about 200 Hz to about 5 kHz, or from about 200 Hz to about 1.2 kHz, or from about 200 Hz to about 1 kHz, or from about 500 Hz to about 20 kHz, or from about 500 Hz to about 1.2 kHz, or from about 500 Hz to about 1 kHz, or about 50 Hz, about 100 Hz, about 200 Hz, about 300 Hz, about 400 Hz, about 500 Hz, about 600 Hz, about 700 Hz, about 800 Hz, about 900 Hz, or about 1 kHz. In particular embodiments, representative current amplitudes for the therapy signal are from 0.1 mA to 20 mA, or 0.5 mA to 10 mA, or 0.5 mA to 7 mA, or 0.5 mA to 5 mA. Representative pulse widths range from about 10 microseconds to about 2.5 milliseconds, about 10 microseconds to about 1 millisecond, about 10 to about 666 microseconds, about 10 to about 333 microseconds, about 10 to about 166 microseconds, about 25 to about 166 microseconds, about 20 to about 100 microseconds, about 30 to about 100 microseconds, about 30 to about 40 microseconds, about 10 to about 50 microseconds, about 20 to about 40 microseconds, about 25 to about 35 microseconds, about 30 to about 35 microseconds, and about 30 microseconds. Duty cycles can range from about 10% to about 100%, and in a particular duty cycle, signals are delivered for 20 seconds and interrupted for 2 minutes (an approximate 14% duty cycle). In other embodiments, these parameters can have other suitable values. Other suitable parameters and other therapy features are disclosed in the following materials, each of which is incorporated by reference: U.S. Patent Application Publication No. US2009/0204173; U.S. Patent Application Publication No. US2014/0296936; and U.S. Patent Application Publication No. US2010/0274314.

In some embodiments, the electrical signals described herein do not produce paresthesia when delivered to the patient, and can therefore be referred to as "non-paresthesia producing electrical signals" or "paresthesia-free electrical signals." This is independent of whether the patient is suffering from neuropathy-induced paresthesia (e.g., paresthesia or tingling caused by a neuropathy as opposed to paresthesia induced by the electrical signal). Accordingly, in some embodiments a paresthesia-free signal may be administered to a patient suffering from neuropathy induced paresthesia. Indeed, as set forth above, in some embodiments the electrical signals provided herein can even reduce neuropathy-induced paresthesia. Thus, in some embodiments, the electrical signals (1) do not induce paresthesia in the patient, and (2) reduce naturally occurring paresthesia.

Paresthesia-free signals may have combinations of frequency, pulse widths, amplitudes, and/or duty cycles that cause the signal to be below a patient's perception threshold. For example, paresthesia-free electrical signals may have a frequency of between about 1 Hz and about 100 kHz, or between about 200 Hz and 100 kHz, or between about 1.2 kHz and about 100 kHz. As another example, paresthesia-free electrical signals may be delivered in discrete bursts, separated by quiescent periods in which the electrical signal is not delivered. Additional examples of paresthesia-free electrical signals are described in U.S. Patent Application Publication No. US2010/0274314, previously incorporated by reference herein. In other embodiments, the electrical signals described herein may induce paresthesia when delivered to the patient.

7.0 Representative Examples

The following examples are provided to further illustrate embodiments of the present technology and are not to be interpreted as limiting the scope of the present technology. To the extent that certain embodiments or features thereof are mentioned, it is merely for purposes of illustration and, unless otherwise specified, is not intended to limit the present technology. It will be understood that many variations can be made in the procedures described herein while still remaining within the bounds of the present technology. Such variations are intended to be included within the scope of the presently disclosed technology.

1. A method of treating a patient having sensation loss associated with diabetic neuropathy, the method comprising:
programming a signal generator to deliver, via at least one implanted signal delivery element, a paresthesia-free electrical signal having a frequency within a frequency range of from about 1.2 kHz to about 100 kHz to the patient's spinal cord,
wherein the paresthesia-free electrical signal activates a first subset of neurons within the spinal cord to modify a state of a second subset of neurons and thereby increase afferent neural activity generated in the second subset of neurons in response to a sensory input.

2. The method of example 1 wherein the activated first subset of neurons modify the state of the second subset of neurons by reducing pathological neural activity within the second subset of neurons.

3. The method of example 1 or example 2 wherein the first subset of neurons includes inhibitory interneurons, and wherein the second subset of neurons includes central afferent transmission neurons and/or peripheral afferent transmission neurons.

4. The method of example 3 wherein the second subset of neurons includes central afferent projection neurons.

5. The method of any of examples 1-4 wherein the first subset of neurons include non-adapting neurons.

6. The method of any of examples 1-5 wherein the second subset of neurons includes adapting neurons.

7. The method of any of examples 1-6 wherein the electrical signal increases the afferent neural activity induced by the sensory input in the second subset of neurons by at least 50% relative to an afferent neural activity induced by the sensory input in the second subset of neurons in the absence of the electrical signal.

8. The method of any of examples 1-6 wherein the electrical signal increases the afferent neural activity induced by the sensory input in the second subset of neurons by at least 100% relative to an afferent neural activity induced by the sensory input in the second subset of neurons in the absence of the electrical signal.

9. The method of any of examples 1-8 wherein the increased afferent neural activity enables the patient to perceive the sensory input.

10. The method of any of examples 1-9 wherein the frequency range is from about 5 kHz to about 15 kHz.

11. The method of any of examples 1-10 wherein the paresthesia-free electrical signal has:
a pulse width in a pulse width range of from about 10 seconds to about 333 microsecond; and
an amplitude in an amplitude range of from about 0.5 mA to about 10 mA.

12. The method of any of examples 1-11 wherein programming the signal generator is performed at least partially in response to the patient having the sensation loss.

13. The method of any of examples 1-12, further comprising:
identifying abnormal neural activity in the second subset of neurons in the absence of the paresthesia-free electrical signal,
wherein programming the signal generator to deliver the paresthesia-free electrical signal is performed at least partially in response to identifying the abnormal neural activity in the second subset of neurons.

14. A method of treating a patient having sensation loss associated with diabetic neuropathy, the method comprising:
programming a signal generator to deliver, via at least one implanted signal delivery element, a paresthesia-free electrical signal having a frequency within a frequency range of from about 1.2 kHz to about 100 kHz to the patient's spinal cord,
wherein the paresthesia-free electrical signal (a) reduces pathological neural activity in the patient, and (b) enhances transmission of afferent neural signals generated in response to a sensory input, thereby at least partially restoring the sensation that was lost in association with the diabetic neuropathy.

15. The method of example 14 wherein, by reducing the pathological neural activity in the patient, the paresthesia-free electrical signal enables the afferent neural signals generated in response to the sensory input to be propagated to the patient's sensory cortex.

16. The method of example 14 or example 15 wherein the pathological neural activity is present in a second subset of neurons, and wherein the paresthesia-free electrical signal activates a first subset of neurons, different than the second subset of neurons, to reduce the pathological neural activity in the second subset of neurons.

17. The method of example 16 wherein the first subset of neurons includes inhibitory interneurons, and wherein the second subset of neurons includes peripheral and/or central afferent transmission neurons.

18. The method of any of examples 14-17 wherein the frequency range is from about 5 kHz to about 15 kHz, and wherein the paresthesia-free electrical signal has a pulse width in a pulse width range of from about 20 microseconds to about 100 microseconds and an amplitude within an amplitude range of from about 0.5 mA to about 10 mA.

19. The method of any of examples 14-18 wherein programming the signal generator is performed at least partially in response to the patient having the pathological neural activity.

20. A method of treating a patient having sensation loss associated with diabetic neuropathy, the method comprising:
    delivering, via at least one implanted signal delivery element, a paresthesia-free electrical signal having a frequency within a frequency range of from about 1.2 kHz to about 100 kHz to the patient's spinal cord,
    wherein the paresthesia-free electrical signal (a) reduces pathological neural activity in the patient, and (b) enhances transmission of afferent neural signals generated in response to a sensory input, thereby at least partially restoring the sensation that was lost in association with the diabetic neuropathy.

21. The method of example 20 wherein the paresthesia-free electrical signal enables the afferent neural signal generated in response to the sensory input to be propagated to the patient's sensory cortex by reducing the pathological neural activity in the patient.

22. The method of example 20 or example 21 wherein the paresthesia-free electrical signal activates a first subset of neurons, and wherein the activation of the first subset of neurons reduces the pathological neural activity in a second subset of neurons, different than the first subset of neurons.

23. The method of example 22 wherein the first subset of neurons includes inhibitory interneurons, and wherein the second subset of neurons includes peripheral and/or central afferent transmission neurons.

24. The method of any of examples 20-23 wherein the frequency range is from about 5 kHz to about 15 kHz, and wherein the paresthesia-free electrical signal has a pulse width in a pulse width range of from about 20 microseconds to about 100 microseconds and an amplitude within an amplitude range of from about 0.5 mA to about 10 mA.

25. The method of any of examples 20-24, further comprising:
    identifying that the patient has pathological neural activity contributing to the patient's sensation loss before delivering the paresthesia-free electrical,
    wherein delivering the paresthesia-free electrical signal is performed at least partially in response to identifying that the patient has the pathological neural activity contributing to the patient's sensation loss.

26. A patient treatment system for treating sensation loss in a patient, the system comprising:
    an implantable signal delivery element positionable proximate a patient's spinal cord region; and
    a signal generator having a controller programmed with instructions that, when executed, cause the signal generator to:
        deliver, via the implantable signal delivery element, a paresthesia-free electrical signal having a frequency within a frequency range of from about 1.2 kHz to about 100 kHz to the patient's spinal cord,
        wherein the paresthesia-free electrical signal (a) reduces pathological neural activity in the patient, and (b) enhances transmission of afferent neural signals generated in response to a sensory input, thereby at least partially restoring the lost sensation.

27. The system of example 26 wherein, by reducing the pathological neural activity in the patient, the paresthesia-free electrical signal enables the afferent neural signals generated in response to the sensory input to be propagated to the patient's sensory cortex.

28. The system of example 26 or example 27 wherein the pathological neural activity is present in a second subset of neurons, and wherein the paresthesia-free electrical signal activates a first subset of neurons, different than the second subset of neurons, to reduce the pathological neural activity in the second subset of neurons.

29. The system of example 28 wherein the first subset of neurons includes inhibitory interneurons, and wherein the second subset of neurons includes peripheral and/or central afferent transmission neurons.

30. The system of any of examples 26-29 wherein the frequency range is from about 5 kHz to about 15 kHz, and wherein the paresthesia-free electrical signal has a pulse width in a pulse width range of from about 20 microseconds to about 100 microseconds and an amplitude within an amplitude range of from about 0.5 mA to about 10 mA.

31. A patient treatment system for treating sensation loss in a patient, the system comprising:
    an implantable signal delivery element positionable proximate a patient's spinal cord region; and
    a signal generator having a controller programmed with instructions that, when executed, cause the signal generator to:
        deliver, via the implantable signal delivery element, a paresthesia-free electrical signal having a frequency within a frequency range of from about 1.2 kHz to about 100 kHz to the patient's spinal cord,
        wherein the paresthesia-free electrical signal activates a first subset of neurons within the spinal cord to modify a state of a second subset of neurons and thereby increase afferent neural activity generated in the second subset of neurons in response to a sensory input.

32. The system of example 31 wherein the activated first subset of neurons modify the state of the second subset of neurons by reducing pathological neural activity within the second subset of neurons.

33. The system of example 31 or example 32 wherein the first subset of neurons includes inhibitory interneurons.

34. The system of any of examples 31-33 wherein the second subset of neurons includes central afferent transmission neurons.

35. The system of example 34 wherein the central afferent transmission neurons include projection neurons.

36. The system of any of examples 31-33 wherein the second subset of neurons includes peripheral afferent neurons.

37. The system of any of examples 31-36 wherein the electrical signal increases the afferent neural activity induced by the sensory input in the second subset of neurons by at least 50% relative to an afferent neural activity induced by the sensory input in the second subset of neurons in the absence of the electrical signal.

38. The system of any of examples 31-36 wherein the electrical signal increases the afferent neural activity induced by the sensory input in the second subset of neurons by at least 100% relative to an afferent neural activity induced by the sensory input in the second subset of neurons in the absence of the electrical signal.

39. The system of any of examples 31-38 wherein the increased afferent neural activity enables the patient to perceive the sensory input.

40. The system of any of examples 31-39 wherein the frequency range is from about 5 kHz to about 15 kHz.

41. The system of any of examples 31-40 wherein the paresthesia-free electrical signal has:
 a pulse width in a pulse width range of from about 10 seconds to about 333 microsecond; and
 an amplitude in an amplitude range of from about 0.5 mA to about 10 mA.

42. A method for treating a patient having sensation loss, via spinal cord stimulation, the method comprising:
 directing an electrical signal to the patient's spinal cord region via a signal delivery element implanted at or proximate the patient's spinal cord region,
 wherein the electrical signal has a frequency within a frequency range of from 200 Hz to 100 kHz, and
 wherein the electrical signal increases afferent neural activity induced via a sensory input.

43. The method of example 42 wherein—
 the electrical signal activates a first subset of neurons,
 the sensory input activates a second subset of neurons different than the first subset, and
 the increased afferent neural activity occurs in the second subset of neurons.

44. The method of example 43 wherein the first subset of neurons include inhibitory interneurons.

45. The method of example 43 or example 44 wherein the second subset of neurons include peripheral afferent neurons.

46. The method of example 43 or example 44 wherein the second subset of neurons include central afferent transmission neurons.

47. The method of example 46 wherein the central afferent transmission neurons include projection neurons.

48. The method of any of examples 42-47 wherein the electrical signal increases the afferent neural activity induced by the sensory input by at least 50% relative to an afferent neural activity induced in the absence of the electrical signal.

49. The method of any of examples 42-47 wherein the electrical signal increases the afferent neural activity induced by the sensory input by at least 100% relative to an afferent neural activity induced by the sensory input in the absence of the electrical signal.

50. The method of any of examples 42-49 wherein the increased afferent neural activity enables the patient to perceive the sensory input.

51. The method of any of examples 42-50 wherein the frequency range is from about 1.2 kHz to about 100 KHz.

CONCLUSION

From the foregoing, it will be appreciated that specific embodiments of the disclosed technology have been described herein for purposes of illustration, but that various modifications may be made without deviating from the technology. Certain aspects of the technology described in the context of particular embodiments may be combined or eliminated in other embodiments. Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. The following examples provide further representative embodiments of the presently disclosed technology.

As used herein, the phrase "and/or," as in "A and/or B" refers to A alone, B alone, and A and B. To the extent any materials incorporated by reference herein conflict with the present disclosure, the present disclosure controls.

We claim:

1. A method of treating a patient having sensation loss associated with diabetic neuropathy, the patient having a first subset of neurons and a second subset of neurons, with at least the second subset of neurons demonstrating a pathological afferent neural response to a sensory input, the method comprising:
 at least partially in response to identifying that the second subset of neurons demonstrate the pathological afferent neural response to a sensory input, programming a signal generator to deliver, via at least one implanted signal delivery element, a paresthesia-free electrical signal having a frequency within a frequency range of from about 200 Hz to about 100 kHz to the patient's spinal cord,
 wherein the paresthesia-free electrical signal activates one or more neurons of the first subset of neurons within the spinal cord to modify a state of one or more neurons of the second subset of neurons and thereby increase afferent neural activity generated in the one or more neurons of the second subset of neurons in response to a sensory input.

2. The method of claim 1 wherein the activated one or more neurons of the first subset of neurons modify the state of the one or more neurons of the second subset of neurons by reducing pathological neural activity within the one or more neurons of the second subset of neurons.

3. The method of claim 1 wherein the first subset of neurons includes inhibitory interneurons, and wherein the second subset of neurons includes central afferent transmission neurons and/or peripheral afferent transmission neurons.

4. The method of claim 3 wherein the one or more neurons of the second subset of neurons includes central afferent projection neurons.

5. The method of claim 1 wherein the one or more neurons of the first subset of neurons include non-adapting neurons.

6. The method of claim 1 wherein the one or more neurons of the second subset of neurons includes adapting neurons.

7. The method of claim 1 wherein the electrical signal increases the afferent neural activity induced by the sensory input in the one or more neurons of the second subset of neurons by at least 50% relative to an afferent neural activity induced by the sensory input in the one or more neurons of the second subset of neurons in the absence of the electrical signal.

8. The method of claim 1 wherein the electrical signal increases the afferent neural activity induced by the sensory input in the one or more neurons of the second subset of neurons by at least 100% relative to an afferent neural activity induced by the sensory input in the one or more neurons of the second subset of neurons in the absence of the electrical signal.

9. The method of claim 1 wherein the increased afferent neural activity enables the patient to perceive the sensory input.

10. The method of claim 1 wherein the frequency range is from about 3 kHz to about 20 KHz.

11. The method of claim 1 wherein the paresthesia-free electrical signal has:
    a pulse width in a pulse width range of from about 10 seconds to about 333 microsecond; and
    an amplitude in an amplitude range of from about 0.5 mA to about 10 mA.

12. The method of claim 1, further comprising:
    identifying that the second subset of neurons demonstrate the pathological afferent neural response to the sensory input, in the absence of the paresthesia-free electrical signal.

13. A method of treating a patient with diabetic neuropathy and identified as having pathological neural activity causing a reduced transmission of afferent neural signals generated in response to a sensory input, the method comprising:
    programming a signal generator to deliver, via at least one implanted signal delivery element, a paresthesia-free electrical signal having a frequency within a frequency range of from about 200 Hz to about 100 kHz to the to the spinal cord of the patient identified as having the pathological neural activity and reduced transmission of afferent neural signals,
    wherein the paresthesia-free electrical signal (a) reduces the pathological neural activity in the patient, and (b) enhances the transmission of afferent neural signals generated in response to a sensory input, thereby at least partially restoring sensation that was lost in association with the diabetic neuropathy.

14. The method of claim 13 wherein, by reducing the pathological neural activity in the patient, the paresthesia-free electrical signal enables the afferent neural signals generated in response to the sensory input to be propagated to the patient's sensory cortex.

15. The method of claim 13 wherein the pathological neural activity is present in a second subset of neurons, and wherein the paresthesia-free electrical signal activates a first subset of neurons, different than the second subset of neurons, to reduce the pathological neural activity in the second subset of neurons.

16. The method of claim 15 wherein the first subset of neurons includes inhibitory interneurons, and wherein the second subset of neurons includes peripheral and/or central afferent transmission neurons.

17. The method of claim 13 wherein the frequency range is from about 3 kHz to about 20 KHz, and wherein the paresthesia-free electrical signal has a pulse width in a pulse width range of from about 20 microseconds to about 100 microseconds and an amplitude within an amplitude range of from about 0.5 mA to about 10 mA.

18. The method of claim 13 wherein programming the signal generator is performed at least partially in response to the patient having the pathological neural activity.

19. A method of treating a patient having diabetic neuropathy and identified as having pathological neural activity causing a reduced transmission of afferent neural signals generated in response to a sensory input, the method comprising:
    delivering, via at least one implanted signal delivery element, a paresthesia-free electrical signal having a frequency within a frequency range of from about 200 Hz to about 100 kHz to spinal cord of the patient identified as having the pathological neural activity and reduced transmission of afferent neural signals,
    wherein the paresthesia-free electrical signal (a) reduces the pathological neural activity in the patient, and (b) enhances the transmission of afferent neural signals generated in response to a sensory input, thereby at least partially restoring sensation that was lost in association with the diabetic neuropathy.

20. The method of claim 19 wherein the paresthesia-free electrical signal enables the afferent neural signal generated in response to the sensory input to be propagated to the patient's sensory cortex by reducing the pathological neural activity in the patient.

21. The method of claim 19 wherein the frequency range is from about 3 kHz to about 20 KHz, and wherein the paresthesia-free electrical signal has a pulse width in a pulse width range of from about 20 microseconds to about 100 microseconds and an amplitude within an amplitude range of from about 0.5 mA to about 10 mA.

22. The method of claim 19, further comprising:
    identifying that the patient has pathological neural activity contributing to the patient's sensation loss before delivering the paresthesia-free electrical,
    wherein delivering the paresthesia-free electrical signal is performed at least partially in response to identifying that the patient has the pathological neural activity contributing to the patient's sensation loss.

23. A method of treating a patient having sensation loss associated with diabetic neuropathy, the patient having inhibitory interneurons and afferent transmission neurons, with at least the afferent transmission neurons demonstrating a pathological afferent neural response to a sensory input, the method comprising:
    at least partially in response to identifying that the afferent transmission neurons demonstrate the pathological afferent neural response to a sensory input, programming a signal generator to deliver, via at least one implanted signal delivery element, a paresthesia-free electrical signal having a frequency within a frequency range of from about 200 Hz to about 100 kHz to the patient's spinal cord,
    wherein the paresthesia-free electrical signal activates one or more of the inhibitory interneurons within the spinal cord to modify a state of one or more of the afferent transmission neurons and thereby increase afferent neural activity generated in the one or more afferent transmission neurons in response to a sensory input.

24. The method of claim 23 wherein the one or more afferent transmission neurons include central afferent transmission neurons.

25. The method of claim 23 wherein the one or more afferent transmission neurons include peripheral afferent transmission neurons.

26. The method of claim 23 wherein the paresthesia-free electrical signal has a pulse width in a pulse width range of from about 10 microseconds to about 333 microseconds and an amplitude within an amplitude range of from about 0.1 mA to about 20 mA.

* * * * *